US006468795B1

(12) United States Patent
Watt

(10) Patent No.: US 6,468,795 B1
(45) Date of Patent: Oct. 22, 2002

(54) ANTISENSE MODULATION OF APAF-1 EXPRESSION

(75) Inventor: Andrew T. Watt, Vista, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/690,364

(22) Filed: Oct. 16, 2000

(51) Int. Cl.[7] .......................... C12Q 1/68; C07H 21/04; C12N 15/85
(52) U.S. Cl. .......................... 435/375; 435/6; 435/91.1; 435/325; 435/366; 536/23.1; 536/24.31; 536/24.33; 536/24.5
(58) Field of Search .......................... 435/6, 366, 375, 435/325; 536/23.1, 24.5; 514/44

(56) References Cited

FOREIGN PATENT DOCUMENTS

| WO | WO 98/55615 | 12/1998 |
|----|-------------|---------|
| WO | WO 99/65937 | 12/1999 |

OTHER PUBLICATIONS

D.D.F. Ma et al., Synthetic oligonucleotides as therapeutics: the coming of age, Biotechnology Annual Review, vol. 5, pp. 155–196.*
Kuang–Yu Jen et al., Suppression of Gene Expression by Targeted Disruption of Messenger RNA: Available Options and Current strategies, Stem Cells, 2000, 18, pp. 307–319.*
Andrea D. Branch, A good antisense molecule is hard to find, TIBS –Feb. 23, 1998, pp. 45–50.*
W. Michael Flanagan et al., Cellular pentration and antisense activity by a phenoxazine–substituted heptanucleotide, Research, pp. 1–5.*
C. Frank Bennett et al., Pharmacology of Antisense Therapeutic Agents, pp. 13–46.*
Sudhir Agrawal et al.,Antisense therapeutics: is it as simple as compementary base recognition? Molecular Medicine Today, Feb. 2000, vol. 6, pp. 72–81.*
Douglas W. Green, M.D. et al., Antisense Oligonucleotides: An Evolving Technology for the Modulation of Gene Expression in Human Disease, J. Am. Coll. Surg. pp. 93–105.*
Afford et al., Apoptosis, Mol. Pathol., 2000, 53:55–63.
Bala et al., Genetic analysis of the APAF1 gene in male germ cell tumors [In Process Citation], Genes, Chromosomes & Cancer, 2000, 28:258–268.
Benedict et al., Expression and functional analysis of Apaf–1 isoforms. Extra Wd–40 repeat is required for cytochrome c binding and regulated activation of procaspase–9, Journal of Biological Chemistry, 2000, 275:8461–8468.
Burgess et al., Human skeletal muscle cytosols are refractory to cytochrome c–dependent activation of type–II caspases and lack APAF–1, Cell Death and Differentiation, 1999, 6:256–261.

Cain et al., Apaf–1 oligomerizes into biologically active approximately 700–kDa and inactive approximately 1.4–MDa apoptosome complexes, Journal of Biological Chemistry, 2000, 275:6067–6070.
Cecconi, Apaf1 and the apoptotic machinery, Cell Death and Differentiation, 1999, 6:1087–1098.
Cecconi et al., Apaf1 (CED–4 homolog) regulates programmed cell death in mammalian development, Cell, 1998, 94:727–737.
Hahn et al., Three new types of Apaf–1 in mammalian cells, Biochemical and Biophysical Research Communications, 1999, 261:746–749.
Hausmann et al., Pro–apoptotic apoptosis protease–activating factor 1 (Apaf–1) has a cytoplasmic localization distinct from Bcl–1 or Bcl–x(L), Journal of Cell Biology, 2000, 149:623–634.
Honarpour et al., Adult Apaf–1–deficient mice exhibit male infertility, Cevelopmental Biology, 2000, 218:248–258.
Hu et al., Role of cytochrome c and dATP/ATP hydrolysis in Apaf–1–mediated caspase–9 activation and apoptosis, The Embo Journal, 1999, 18:3586–3595.
Kim et al., Assignment of apoptotic protease activating factor–1 gene (APAF1) to human chromosome band 12q23 by fluorescence in situ hybridization, Cytogenet. Cell Genet., 1999 87:252–253.
Perkins et al., Overexpression of Apaf–1 promotes apoptosis of untreated and paclitaxel–or etoposide–treated HL–60 cells, Cancer Research, 1998, 58:4561–4566.
Saleh et al., Cytochrome c and dATP–mediated oligomerization of Apaf–1 is a prerequisite for procaspase–9 activation, Journal of Biological Chemistry, 1999, 274:17941–17945.
Soengas et al., Apaf–1 and caspase–9 in p53–dependent apoptosis and tumor inhibition, Science, 1999, 284:156–159.
Yamamoto et al., Frameshift mutations in Fas, Apaf–1, and Bcl–10 in gastro–intestinal cancer of the microsatellite mutator phenotype, Cell Death and Differentiation, 2000, 7:238–239.
Zou et al., Apaf–1, a human protein homologous to C. elegans CED–4, participates in cytochrome c–dependent activation of caspase–3, Cell, 1997, 90:405–413.
Zou et al., An APAF–1.cytochrome c multimeric complex is a functional apoptosome that activates procaspase–9, Journal of Biological Chemistry, 1999, 274:11549–11556.

* cited by examiner

Primary Examiner—John L. LeGuyader
Assistant Examiner—M Schmidt
(74) Attorney, Agent, or Firm—Licata & Tyrrell P.C.

(57) ABSTRACT

Antisense compounds, compositions and methods are provided for modulating the expression of Apaf-1. The compositions comprise antisense compounds, particularly antisense oligonucleotides, targeted to nucleic acids encoding Apaf-1. Methods of using these compounds for modulation of Apaf-1 expression and for treatment of diseases associated with expression of Apaf-1 are provided.

26 Claims, No Drawings

ANTISENSE MODULATION OF APAF-1 EXPRESSION

FIELD OF THE INVENTION

The present invention provides compositions and methods for modulating the expression of Apaf-1. In particular, this invention relates to compounds, particularly oligonucleotides, specifically hybridizable with nucleic acids encoding Apaf-1. Such compounds have been shown to modulate the expression of Apaf-1.

BACKGROUND OF THE INVENTION

Apoptosis, or programmed cell death, is a naturally occurring process that has been strongly conserved during evolution to prevent uncontrolled cell proliferation. This form of cell suicide plays a crucial role in ensuring the development and maintenance of multicellular organisms by eliminating superfluous or unwanted cells. However, if this process goes awry becoming overstimulated, cell loss and degenerative disorders including neurological disorders such as Alzheimers, Parkinsons, ALS, retinitis pigmentosa and blood cell disorders can result. Stimuli which can trigger apoptosis include growth factors such as tumor necrosis factor (TNF), Fas and transforming growth factor beta (TGFβ), neurotransmitters, growth factor withdrawal, loss of extracellular matrix attachment and extreme fluctuations in intracellular calcium levels (Afford and Randhawa, Mol. Pathol., 2000, 53, 55–63).

Alternatively, insufficient apoptosis, triggered by growth factors, extracellular matrix changes, CD40 ligand, viral gene products neutral amino acids, zinc, estrogen and androgens, can contribute to the development of cancer, autoimmune disorders and viral infections (Afford and Randhawa, Mol. Pathol., 2000, 53, 55–63). Consequently, apoptosis is regulated under normal circumstances by the interaction of gene products that either induce or inhibit cell death and several gene products which modulate the apoptotic process have now been identified.

Apoptotic protease activating factor 1 (also known as Apaf-1) is the human homolog of the C. elegans gene, ced-4, originally purified and cloned from HeLa cell cytosol (Zou et al., Cell, 1997, 90, 405–413). Disclosed in the PCT Publication WO 98/55615 are the protein and nucleic acid sequences of Apaf-1 as are antibodies to the protein, host cells which express a vector encoding the nucleic acid sequence of Apaf-1, transgenic and knock-out animals and methods to detect Apaf-1 modulating compounds. Generally disclosed is an isolated nucleic acid comprising a nucleotide which would hybridize to Apaf-1 under stringent conditions (Zou et al., 1998).

Characterization of the protein has revealed that Apaf-1 contains a domain structure with defined regions of homology to existing proteins including WD repeats, and caspase-related domains (Zou et al., Cell, 1997, 90, 405–413). Tissue localization studies have demonstrated that Apaf-1 can be found in most tissues (Zou et al., Cell, 1997, 90, 405–413), however there is debate on the presence of Apaf-1 in skeletal muscle (Burgess et al., Cell Death and Differentiation, 1999, 6, 256–261). Within the cell, Apaf-1 is localized to the cytosol (Hausmann et al., Journal of Cell Biology, 2000, 149, 623–634) and at least three variants of the protein have been identified to date. Hahn et al. describe three novel forms of Apaf-1 isolated from six lymphoma cell lines, three non-lymphoid tumor cell lines, peripheral blood lymphocytes, and in tissues from heart, kidney and liver (Hahn et al., Biochemical and Biophysical Research Communications, 1999, 261, 746–749).

Others have also identified alternate forms of Apaf-1 resulting from differential splicing events (Benedict et al., Journal of Biological Chemistry, 2000, 275, 8461–8468; Hu et al., The Embo Journal, 1999, 18, 3586–3595). Characterization of these variants demonstrated that longer forms of the protein containing an extra WD repeat were required to activate the apoptotic cascade orchestrated by caspases (Benedict et al., Journal of Biological Chemistry, 2000, 275, 8461–8468). Disclosed in the PCT publication WO 99/65937 are the nucleic acid sequence of Apaf-1 including truncated variants of Apaf-1 which may oligomerize with members of the caspase family as are host cells which express a vector encoding the nucleic acid sequence of Apaf-1, and methods to detect inhibitors of apoptosis and Apaf-1 modulating compounds. Generally disclosed is an isolated nucleic acid comprising a nucleotide which would hybridize to Apaf-1 under stringent conditions (Alnemri, 1999).

Since its isolation, Apaf-1 has been shown to play a critical role in the regulation of apoptosis through multiple signaling pathways reviewed in (Cecconi, Cell Death and Differentiation, 1999, 6, 1087–1098). Primarily Apaf-1 acts through cytochrome c-mediated caspase activation (Saleh et al., Journal of Biological Chemistry, 1999, 274, 17941–17945). Upon release of cytochrome c from the mitochondria and in the presence of DATP (deoxy ATP), Apaf-1 oligomerizes and forms a complex with procaspase-9 (Cain et al., Journal of Biological Chemistry, 2000, 275, 6067–6070; Zou et al., Journal of Biological Chemistry, 1999, 274, 11549–11556). In turn, procaspase-9 is cleaved into its active form, leading to the activation of caspase-3, the major caspase in the apoptotic pathway. Overexpression of Apaf-1 has been shown to increase sensitivity of human myeloid leukemia HL-60 cells to the apoptosis-inducing agents paclitaxel and etoposide (Perkins et al., Cancer Research, 1998, 58, 4561–4566).

Although Apaf-1 has been localized to chromosome 12q23, a region recurrently deleted in male germ cell tumors, genetic analysis has shown that Apaf-1 is not a tumor suppressor gene candidate (Bala et al., Genes, Chromosomes & Cancer, 2000, 28, 258–268; Kim et al., Cytogenet. Cell Genet., 1999, 87, 252–253). Expression of Apaf-1, nonetheless has been associated with several types of cancers. Frameshift mutations in the Apaf-1 gene have been suggested to provide a survival advantage to some tumor types (Yamamoto et al., Cell Death and Differentiation, 2000, 7, 238–239) and mouse embryonic cells lacking Apaf-1 and caspase-9 were shown to be resistant to apoptotic stimuli (Soengas et al., Science, 1999, 284, 156–159). The majority of homozygous knockout mice lacking Apaf-1 die early in embryogenesis and show reduced apoptosis leading to many morphological abnormalities. In the mice reaching maturity, the adult heterozygote males exhibit infertility (Cecconi et al., Cell, 1998, 94, 727–737; Honarpour et al., Cevelopmental Biology, 2000, 218, 248–258).

Collectively, these data suggest that modulation of Apaf-1 would render opportunity to treat patients with various cancers and deregulated apoptotic pathologic conditions.

Strategies aimed at modulating Apaf-1 function have involved the use of antibodies and gene knockouts in mice. However, these strategies are untested as therapeutic protocols and consequently there remains a long felt need for agents capable of effectively inhibiting Apaf-1 function.

Antisense technology is emerging as an effective means for reducing the expression of specific gene products and may therefore prove to be uniquely useful in a number of therapeutic, diagnostic, and research applications for the modulation of Apaf-1.

The present invention provides compositions and methods for modulating Apaf-1 expression, including modulation of the truncated forms, including splice variants of Apaf-1.

SUMMARY OF THE INVENTION

The present invention is directed to compounds, particularly antisense oligonucleotides, which are targeted to a nucleic acid encoding Apaf-1, and which modulate the expression of Apaf-1. Pharmaceutical and other compositions comprising the compounds of the invention are also provided. Further provided are methods of modulating the expression of Apaf-1 in cells or tissues comprising contacting said cells or tissues with one or more of the antisense compounds or compositions of the invention. Further provided are methods of treating an animal, particularly a human, suspected of having or being prone to a disease or condition associated with expression of Apaf-1 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding Apaf-1, ultimately modulating the amount of Apaf-1 produced. This is accomplished by providing antisense compounds which specifically hybridize with one or more nucleic acids encoding Apaf-1. As used herein, the terms "target nucleic acid" and "nucleic acid encoding Apaf-1" encompass DNA encoding Apaf-1, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of Apaf-1. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding Apaf-1. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Apaf-1, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'–5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3$^1$-most internucleotide linkage i.e. a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 3' or 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687, 808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds.,*Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al.,*Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of Apaf-1 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding Apaf-1, enabling sandwich and other assays to easily be constructed to exploit this fact. Hybridization of the antisense oligonucleotides of the invention with a nucleic acid encoding Apaf-1 can be detected by means known in the art. Such means may include conjugation of an enzyme to the oligonucleotide, radiolabelling of the oligonucleotide or any other suitable detection means. Kits using such detection means for detecting the level of Apaf-1 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate,. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly (methylcyanoacrylate), poly(ethylcyanoacrylate), poly (butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no hermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases posess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and triglycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626)

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4' isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-Alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3' phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-Arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in CHCl3 (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH$_2$Cl$_2$ (1 L) Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(Dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-Phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at −10° C. to 0° C. After 1 h the mixture was filtered, the filtrate was washed with ice cold CH$_2$Cl$_2$ and the combined organic phase was washed with water, brine and dried over anhydrous Na$_2$SO$_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in CH$_2$Cl$_2$). Aqueous NaHCO$_3$ solution (5%, 10 mL) was added and extracted with ethyl acetate (2×20 mL). Ethyl acetate phase was dried over anhydrous Na$_2$SO$_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% NaHCO$_3$ (25 mL) solution was added and extracted with ethyl acetate (2×25 mL). Ethyl acetate layer was dried over anhydrous Na$_2$SO$_4$ and evaporated to dryness. The residue obtained was purified by flash column chromatography and eluted with 5% MeOH in CH$_2$Cl$_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in CH$_2$Cl$_2$). Solvent was removed under vacuum and the residue placed on a flash column and eluted with 10% MeOH in CH$_2$Cl$_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over P$_2$O$_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH$_2$Cl$_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-Dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P$_2$O$_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-Isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'—O—CH$_2$—O—CH$_2$—N(CH$_2$)$_2$, or 2'-DMAEOE nucleoside amidites) are prepared as follows. Other nucleoside amidites are prepared similarly.

2'-O-[2(2-N,N-Dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O$^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-Dimethoxytrityl-2'-O-[2(2-N,N-dimethylaminoethoxy)ethyl)]-5-methyl Uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using $MeOH:CH_2Cl_2:Et_3N$ (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxyl]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl)phosphodiester] chimeric oligonucleotides are prepared as per the above procedure for the 2'-O-methyl chimeric oligonucleotide with the substitution of 2'-O-(methoxyethyl)amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by 31P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3, H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 5 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, VA). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC)

(Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

b.END Cells:

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Apaf-1 Expression

Antisense modulation of Apaf-1 expression can be assayed in a variety of ways known in the art. For example, Apaf-1 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of Apaf-1 can be quantitated in a variety of ways well known in the art, such as immunoprecipitation, Western blot analysis (immunoblotting), ELISA or fluorescence-activated cell sorting (FACS). Antibodies directed to Apaf-1 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758–1764. Other methods for poly(A)+ mRNA isolation are taught in, for example, Ausubel, F.M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96' plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Apaf-1 mRNA Levels

Quantitation of Apaf-1 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMPA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif.. RT-PCR reactions were carried out by adding 25 μL PCR cocktail (1× TAQMAN™ buffer A, 5.5 mM MgCl$_2$, 300 μM each of DATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25uL purified, cellular RNA. The plate is read in a CytoFluor 4000 (PE Applied Biosystems) with excitation at 480 nm and emission at 520 nm.

Probes and primers to human Apaf-1 were designed to hybridize to a human Apaf-1 sequence, using published sequence information (GenBank accession number AF098869, incorporated herein as SEQ ID NO:3). For human Apaf-1 the PCR primers were: forward primer: AGAGCCCTGCACCCCTAATT (SEQ ID NO: 4) reverse primer: TTTGCGCCTAGGTCTTAGTGG (SEQ ID NO: 5) and the PCR probe was: FAM-TCTCCCAGTCTTGTCCCGGCAGTG-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: CAACGGATTTGGTCGTATTGG (SEQ ID NO: 7) reverse primer: GGCAACAATATCCACTTTACCAGAGT (SEQ ID NO: 8) and the PCR probe was: 5' JOE-CGCCTGGTCACCAGGGCTGCT- TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse Apaf-1 were designed to hybridize to a mouse Apaf-1 sequence, using published sequence information (GenBank accession number NM_009684, incorporated herein as SEQ ID NO:10). For mouse Apaf-1 the PCR primers were: forward primer: AAGCAGGAAATAGACGTCGTGTT (SEQ ID NO:11) reverse primer: CAATGAGTTGCAGGCCTCTTATG (SEQ ID NO: 12) and the PCR probe was: FAM-TGTCAACTGCAAGGACCATCGTTTCG-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were: forward primer: GGCAAATTCAACGGCACAGT (SEQ ID NO: 14) reverse primer: GGGTCTCGCTCCTGGAAGCT (SEQ ID NO: 15) and the PCR probe was: 5' JOE-AAGGCCGAGAATGGGAAGCTTGTCATC- TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Apaf-1 mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human Apaf-1, a human Apaf-1 specific probe was prepared by PCR using the forward primer AGAGC-CCTGCACCCCTAATT (SEQ ID NO: 4) and the reverse primer TTTGCGCCTAGGTCTTAGTGG (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse Apaf-1, a mouse Apaf-1 specific probe was prepared by PCR using the forward primer AAGCAG-GAAATAGACGTCGTGTT (SEQ ID NO:11) and the reverse primer CAATGAGTTGCAGGCCTCTTATG (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUAN™ Software V3.3 (Molecular Dynamics, Sunnyvale, Calif.). Data was normalized to GAPDH levels in untreated controls.

Example 15

Antisense Inhibition of Human Apaf-1 Expression by Chimeric Phosphorothioate Oligonucleotides Having 2'-MOE Wings and a Deoxy Gap In accordance with the present invention, a series of oligonucleotides were designed to target different regions of the human Apaf-1 RNA, using published sequences (GenBank accession number AF098869, incorporated herein as SEQ ID NO: 3, GenBank accession number AF149794, incorporated herein as SEQ ID NO: 17, GenBank accession number AF098887, incorporated herein as SEQ ID NO: 18, GenBank accession number AF098889, incorporated herein as SEQ ID NO: 19, GenBank accession number AF098905, incorporated herein as SEQ ID NO: 20, GenBank accession number NM_001160, incorporated herein as SEQ ID NO: 21, and GenBank accession number AA902262, incorporated herein as SEQ ID NO: 22). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human Apaf-1 mRNA levels by quantitative real-time PCR as described in other examples herein. Data are averages from two experiments. If present, "N.D." indicates "no data".

TABLE 1

Inhibition of human Apaf-1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 134982 | Coding | 17 | 323 | caggactgtccttacatacg | 26 | 23 |
| 134983 | Coding | 17 | 2477 | caataggccactagtatgaa | 28 | 24 |
| 134984 | Coding | 17 | 2513 | ctggatggtgctgtgatggc | 74 | 25 |
| 134985 | Coding | 17 | 2519 | acagtactggatggtgctgt | 76 | 26 |
| 134986 | Coding | 17 | 2529 | gggagaagtcacagtactgg | 40 | 27 |
| 134987 | Intron | 3 | 162 | cccaagcctttgcgcctagg | 94 | 28 |
| 134988 | Intron | 3 | 297 | cataacagaattttcttcct | 26 | 29 |
| 134989 | Intron | 18 | 100 | aatgagattccttttagca | 34 | 30 |
| 134990 | Intron | 18 | 265 | tgaacatcttattttcctag | 76 | 31 |
| 134991 | Intron | 18 | 355 | tatagtaatcttcttcggac | 0 | 32 |
| 134992 | Intron | 19 | 141 | aatcctcctggagtgatcgt | 92 | 33 |
| 134993 | Intron | 20 | 37 | atacctcaatggctccattt | 41 | 34 |
| 134994 | Intron | 20 | 364 | gctgaggccggacaatcgct | 85 | 35 |
| 134995 | 5'UTR | 21 | 303 | ccccagggacctccgaaggt | 88 | 36 |
| 134996 | 5'UTR | 21 | 527 | caaccatgagccaagccttt | 83 | 37 |
| 134997 | Start Codon | 21 | 569 | tttgcatccatcttccctca | 89 | 38 |
| 134998 | Coding | 21 | 596 | ctatgttgaagcaaacaatt | 79 | 39 |
| 134999 | Coding | 21 | 602 | gcttctctatgttgaagcaa | 61 | 40 |
| 135000 | Coding | 21 | 646 | tcatgtgatccatgatgta | 75 | 41 |
| 135001 | Coding | 21 | 884 | ggtactccaccttcacacag | 96 | 42 |
| 135002 | Coding | 21 | 1109 | agcccagatttgtcttgttt | 94 | 43 |
| 135003 | Coding | 21 | 1185 | aatattaagtggaagcctct | 87 | 44 |
| 135004 | Coding | 21 | 1241 | agagaccttgggtgtttgcg | 46 | 45 |
| 135005 | Coding | 21 | 1264 | cccaaacatcatccaagatc | 66 | 46 |
| 135006 | Coding | 21 | 1313 | gtaagaagaatctgacactg | 91 | 47 |
| 135007 | Coding | 21 | 1343 | actgaatctgtaacactctt | 69 | 48 |
| 135008 | Coding | 21 | 1349 | cccattactgaatctgtaac | 78 | 49 |
| 135009 | Coding | 21 | 1355 | ttaggacccattactgaatc | 99 | 50 |
| 135010 | Coding | 21 | 1358 | tatttaggacccattactga | 90 | 51 |
| 135011 | Coding | 21 | 1433 | ttcttcatattaacaaaaag | 7 | 52 |
| 135012 | Coding | 21 | 1520 | cgtaaaagtgcaccaattaa | 78 | 53 |
| 135013 | Coding | 21 | 1532 | ttgggaaaatcacgtaaaag | 0 | 54 |
| 135014 | Coding | 21 | 1538 | cagccgattgggaaaatcacg | 88 | 55 |
| 135015 | Coding | 21 | 1579 | tcttaaactgcttattctga | 99 | 56 |
| 135016 | Coding | 21 | 1587 | ccttattctcttaaactgct | 55 | 57 |
| 135017 | Coding | 21 | 1617 | tagagcctcataatcataag | 77 | 58 |
| 135018 | Coding | 21 | 1623 | ttcatctagagcctcataat | 66 | 59 |
| 135019 | Coding | 21 | 1629 | catggcttcatctagagcct | 65 | 60 |
| 135020 | Coding | 21 | 1653 | tctgagcatttcaacactta | 97 | 61 |
| 135021 | Coding | 21 | 1664 | ttgatgtcttctctgagcat | 94 | 62 |
| 135022 | Coding | 21 | 1701 | gtccttctgaaggatggaaa | 30 | 63 |
| 135023 | Coding | 21 | 1729 | tacataacacctttgtaggc | 67 | 64 |
| 135024 | Coding | 21 | 1864 | ctgtaagaaaatctacttga | 17 | 65 |
| 135025 | Coding | 21 | 1870 | tcttctctgtaagaaaatct | 38 | 66 |
| 135026 | Coding | 21 | 2048 | tccagggaaaacattaaagc | 98 | 67 |
| 135027 | Coding | 21 | 2143 | ctgcacaatccttttcatct | 52 | 68 |
| 135028 | Coding | 21 | 2144 | actgcacaatccttttcatc | 43 | 69 |
| 135029 | Coding | 21 | 2184 | gtgtccatttaaagataaaa | 64 | 70 |
| 135030 | Coding | 21 | 2207 | ggaaatggctgtcgtccaag | 89 | 71 |
| 135031 | Coding | 21 | 2219 | tgtacaatattaggaaatgg | 95 | 72 |
| 135032 | Coding | 21 | 2285 | tcctgcttggcctgcagctt | 94 | 73 |
| 135033 | Coding | 21 | 2321 | tttatccattccaggtaaag | 35 | 74 |
| 135034 | Coding | 21 | 2382 | gtaaacagcatctgtgtggg | 61 | 75 |
| 135035 | Coding | 21 | 2426 | ccacaagaagctattctctg | 71 | 76 |
| 135036 | Coding | 21 | 2447 | acctgtaaggttttatcagc | 83 | 77 |
| 135037 | Coding | 21 | 2453 | ttgaacacctgtaaggtttt | 35 | 78 |
| 135038 | Coding | 21 | 2455 | ctttgaacacctgtaaggtt | 59 | 79 |
| 135039 | Coding | 21 | 2643 | atggcagcaattgacttgct | 66 | 80 |
| 135040 | Coding | 24 | 2655 | actgttggtgaaatggcagc | 91 | 81 |
| 135041 | Coding | 21 | 2731 | gacattcttttgattcaaa | 73 | 82 |
| 135042 | Coding | 21 | 2742 | catggtatttcgacattctt | 83 | 83 |
| 135043 | Coding | 21 | 2748 | accaaacatggtatttcgac | 82 | 84 |
| 135044 | Coding | 21 | 2839 | catcccaaagctttaaggtt | 59 | 85 |
| 135045 | Coding | 21 | 2873 | acattaatgcttttcctctc | 84 | 86 |
| 135046 | Coding | 21 | 3127 | tctcccagagcctgattgtc | 24 | 87 |
| 135047 | Coding | 21 | 3364 | gttctaaatctcaatggct | 12 | 88 |
| 135048 | Coding | 21 | 3494 | tgccaattccatacctgaat | 73 | 89 |
| 135049 | Coding | 21 | 3592 | ttccatcaaatgaccaagaa | 55 | 90 |
| 135050 | Coding | 21 | 3736 | aactccagatctttgcagtc | 63 | 91 |
| 135051 | Coding | 21 | 3848 | atttctccattgtcatctcc | 81 | 92 |

TABLE 1-continued

Inhibition of human Apaf-1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 135052 | Coding | 21 | 4006 | cgttccaccacttaatatat | 81 | 93 |
| 135053 | Coding | 21 | 4040 | gtgtagaaggtctgtgagga | 75 | 94 |
| 135054 | Coding | 21 | 4046 | ccatttgtgtagaaggtctg | 92 | 95 |
| 135055 | Stop Codon | 21 | 4150 | aactatttattctaaagtc | 0 | 96 |
| 135056 | 3'UTR | 21 | 5308 | gccaggccagtggctcatat | 31 | 97 |
| 135057 | 3'UTR | 21 | 6761 | cctcttgaccgactgcatga | 91 | 98 |
| 135058 | 3'UTR | 21 | 6989 | gaattttatttttacaaaaa | 35 | 99 |
| 135059 | 5'UTR | 22 | 277 | acactgaggaggacctcaga | 15 | 100 |

As shown in Table 1, SEQ ID NOs 25, 26, 28, 31, 33, 35, 36, 37, 38, 39, 40, 41, 42, 43, 44, 46, 47, 48, 49, 50, 51, 53, 55, 56, 57, 58, 59, 60, 61, 62, 64, 67, 68, 70, 71, 72, 73, 75, 76, 77, 79, 80, 81, 82, 83, 84, 85, 86, 89, 90, 91, 92, 93, 94, 95 and 98 demonstrated at least 50% inhibition of human Apaf-1 expression in this assay and are therefore preferred. The target sites to which these preferred sequences are complementary are herein referred to as "active sites" and are therefore preferred sites for targeting by compounds of the present invention.

Example 16

Antisense Inhibition of Mouse Apaf-1 Expression by Chimeric Phosphorothioate Oligonucleotides Having 2'-MOE Wings and a Deoxy Gap In accordance with the present invention, a second series of oligonucleotides were designed to target different regions of the mouse Apaf-1 RNA, using published sequences (GenBank accession number NM_009684, incorporated herein as SEQ ID NO: 10). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse Apaf-1 mRNA levels by quantitative real-time PCR as described in other examples herein. Data are averages from two experiments. If present, "N.D." indicates "no data".

TABLE 2

Inhibition of mouse Apaf-1 mRNA levels by chimeric phosphorothioate oligonucleotides havini 21-MOE wings and a deoxy gap

| ISIS # | REGION | TARGET SEQ ID NO | TARGET SITE | SEQUENCE | % INHIB | SEQ ID NO |
|---|---|---|---|---|---|---|
| 134983 | Coding | 10 | 3029 | caataggccactagtatgaa | 4 | 24 |
| 134984 | Coding | 10 | 3065 | ctggatggtgctgtgatggc | 36 | 25 |
| 134985 | Coding | 10 | 3071 | acagtactggatggtgctgt | 48 | 26 |
| 134986 | Coding | 10 | 3081 | gggagaagtcacagtactgg | 31 | 27 |
| 134998 | Coding | 10 | 604 | ctatgttgaagcaaacaatt | 44 | 39 |
| 134999 | Coding | 10 | 610 | gcttctctatgttgaagcaa | 17 | 40 |
| 135000 | Coding | 10 | 654 | tcatgtgatccatgatgtag | 49 | 41 |
| 135001 | Coding | 10 | 892 | ggtactccaccttcacacag | 11 | 42 |
| 135002 | Coding | 10 | 1117 | agcccagatttgtcttgttt | 59 | 43 |
| 135003 | Coding | 10 | 1193 | aatattaagtggaagcctct | 44 | 44 |
| 135004 | Coding | 10 | 1249 | agagaccttgggtgtttgcg | 12 | 45 |
| 135005 | Coding | 10 | 1272 | cccaaacatcatccaagatc | 80 | 46 |
| 135006 | Coding | 10 | 1321 | gtaagaagaatctgacactg | 27 | 47 |
| 135007 | Coding | 10 | 1351 | actgaatctgtaacactctt | 19 | 48 |
| 135008 | Coding | 10 | 1357 | cccattactgaatctgtaac | 64 | 49 |
| 135009 | Coding | 10 | 1363 | ttaggacccattactgaatc | 40 | 50 |
| 135011 | Coding | 10 | 1441 | ttcttcatattaacaaaaag | 2 | 52 |
| 135012 | Coding | 10 | 1528 | cgtaaaagtgcaccaattaa | 25 | 53 |
| 135013 | Coding | 10 | 1540 | ttgggaaaatcacgtaaaag | 24 | 54 |
| 135014 | Coding | 10 | 1546 | cagcgattgggaaaatcacg | 65 | 55 |
| 135015 | Coding | 10 | 1587 | tcttaaactgcttattctga | 68 | 56 |
| 135016 | Coding | 10 | 1595 | ccttattctcttaaactgct | 72 | 57 |
| 135017 | Coding | 10 | 1625 | tagagcctcataatcataag | 55 | 58 |
| 135018 | Coding | 10 | 1631 | ttcatctagagcctcataat | 55 | 59 |

TABLE 2-continued

Inhibition of mouse Apaf-1 mRNA levels by chimeric phosphorothioate oligonucleotides havini 21-MOE wings and a deoxy gap

| ISIS # | REGION | TARGET SEQ ID NO | TARGET SITE | SEQUENCE | % INHIB | SEQ ID NO |
|---|---|---|---|---|---|---|
| 135019 | Coding | 10 | 1637 | catggcttcatctagagcct | 54 | 60 |
| 135020 | Coding | 10 | 1661 | tctgagcatttcaacactta | 68 | 61 |
| 135021 | Coding | 10 | 1672 | ttgatgtcttctctgagcat | 51 | 62 |
| 135022 | Coding | 10 | 1709 | gtccttctgaaggatggaaa | 0 | 63 |
| 135024 | Coding | 10 | 1872 | ctgtaagaaaatctacttga | 46 | 65 |
| 135025 | Coding | 10 | 1878 | tcttctctgtaagaaaatct | 36 | 66 |
| 135026 | Coding | 10 | 2056 | tccagggaaaacattaaagc | 60 | 67 |
| 135028 | Coding | 10 | 2152 | actgcacaatccttttcatc | 19 | 69 |
| 135029 | Coding | 10 | 2192 | gtgtccatttaaagataaaa | 30 | 70 |
| 135030 | Coding | 10 | 2215 | ggaaatggctgtcgtccaag | 70 | 71 |
| 135031 | Coding | 10 | 2227 | tgtacaatattaggaaatgg | 26 | 72 |
| 135032 | Coding | 10 | 2293 | tcctgcttggcctgcagctt | 46 | 73 |
| 135033 | Coding | 10 | 2329 | ttatccattccaggtaaag | 14 | 74 |
| 135034 | Coding | 10 | 2390 | gtaaacagcatctgtgtggg | 24 | 75 |
| 135035 | Coding | 10 | 2434 | ccacaagaagctattctctg | 52 | 76 |
| 135036 | Coding | 10 | 2455 | acctgtaaggttttatcagc | 34 | 77 |
| 135037 | Coding | 10 | 2461 | ttgaacacctgtaaggtttt | 29 | 78 |
| 135038 | Coding | 10 | 2463 | ctttgaacacctgtaaggtt | 20 | 79 |
| 135039 | Coding | 10 | 2651 | atggcagcaattgacttgct | 46 | 80 |
| 135040 | Coding | 10 | 2663 | actgttggtgaaatggcagc | 33 | 81 |
| 135041 | Coding | 10 | 2739 | gacattcttttgattcaaa | 43 | 82 |
| 135042 | Coding | 10 | 2750 | catggtatttcgacattctt | 69 | 83 |
| 135043 | Coding | 10 | 2756 | accaaacatggtatttcgac | 68 | 84 |
| 135045 | Coding | 10 | 2881 | acattaatgcttttcctctc | 43 | 86 |
| 135048 | Coding | 10 | 3631 | tgccaattccatacctgaat | 45 | 89 |
| 135049 | Coding | 10 | 3729 | ttccatcaaatgaccaagaa | 38 | 90 |
| 135051 | Coding | 10 | 3985 | atttctccattgtcatctcc | 0 | 92 |
| 135053 | Coding | 10 | 4180 | gtgtagaaggtctgtgagga | 25 | 94 |
| 135954 | Coding | 10 | 4186 | ccatttgtgtagaaggtgtctg | 30 | 95 |

As shown in Table 2, SEQ ID NOs 25, 26, 27, 39, 41, 43, 44, 46, 47, 49, 50, 53, 54, 55, 56, 57, 58, 59, 60, 61, 62, 65, 66, 67, 70, 71, 72, 73, 75, 76, 77, 78, 80, 81, 82, 83, 84, 86, 89, 90, 94 and 95 demonstrated at least 22% inhibition of mouse Apaf-1 expression in this experiment and are therefore preferred. The target sites to which these preferred sequences are complementary are herein referred to as "active sites" and are therefore preferred sites for targeting by compounds of the present invention.

Example 17

Western Blot Analysis of Apaf-1 Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to Apaf-1 is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 19 to 50 nucleobases in length targeted to nucleobases 2477 through 2548 of a nucleic acid molecule encoding human Apaf-1 of SEQ ID NO: 17, nucleobases 303 through 546 of a 5'-untranslated region, or nucleobases 596 through 4065 of a coding region, of a nucleic acid molecule encoding human Apaf-1 of SEQ ID NO: 21, or nucleobases 604 through 4205 of a coding region of a nucleic acid molecule encoding mouse Apaf-1 of SEQ ID NO: 10, wherein said compound specifically hybridizes with one of said regions and inhibits the expression of human or mouse Apaf-1.

2. The compound of claim 1 which is an antisense oligonucleotide.

3. A compound up to 50 nucleobases in length comprising at least a 19 nucleobase portion of SEQ ID NO: 25, 26, 27, 28, 31, 33, 35, 36, 37, 38, 39, 40, 41, 42, 43, 44, 46, 47, 48, 49, 50, 51, 53, 54, 55, 56, 57, 58, 59, 60, 61, 62, 64, 65, 66, 67, 68, 70, 71, 72, 73, 75, 76, 77, 78, 79, 80, 81, 82, 83, 84, 85, 86, 89, 90, 91, 92, 93, 94, 95 or 98 which inhibits the expression of human or mouse Apaf-1.

4. The compound of claim 2 wherein the antisense oligonucleotide comprises at least one modified internucleoside linkage.

5. The compound of claim 4 wherein the modified internucleoside linkage is a phosphorothioate linkage.

6. The compound of claim 2 wherein the antisense oligonucleotide comprises at least one modified sugar moiety.

7. The compound of claim 6 wherein the modified sugar moiety is a 2'-O-methoxyethyl sugar moiety.

8. The compound of claim 2 wherein the antisense oligonucleotide comprises at least one modified nucleobase.

9. The compound of claim 8 wherein the modified nucleobase is a 5-methylcytosine.

10. The compound of claim 2 wherein the antisense oligonucleotide is a chimeric oligonucleotide.

11. A composition comprising the compound of claim 1 and a pharmaceutically acceptable carrier or diluent.

12. The composition of claim 11 further comprising a colloidal dispersion system.

13. The composition of claim 11 wherein the compound is an antisense oligonucleotide.

14. A method of inhibiting the expression of human or mouse Apaf-1 in cells or tissues comprising contacting said cells or tissues in vitro with the compound of claim 1 so that expression of human or mouse Apaf-1 is inhibited.

15. The compound of claim 3 which is an antisense oligonucleotide.

16. The compound of claim 15 wherein the antisense oligonucleotide comprises at least one modified internucleoside linkage.

17. The compound of claim 16 wherein the modified internucleoside linkage is a phosphorothioate linkage.

18. The compound of claim 15 wherein the antisense oligonucleotide comprises at least one modified sugar moiety.

19. The compound of claim 18 wherein the modified sugar moiety is a 2'-O-methoxyethyl sugar moiety.

20. The compound of claim 15 wherein the antisense oligonucleotide comprises at least one modified nucleobase.

21. The compound of claim 20 wherein the modified nucleobase is a 5-methylcytosine.

22. The compound of claim 15 wherein the antisense oligonucleotide is a chimeric oligonucleotide.

23. A composition comprising the compound of claim 3 and a pharmaceutically acceptable carrier or diluent.

24. The composition of claim 23 further comprising a colloidal dispersion system.

25. The composition of claim 23 wherein the compound is an antisense oligonucleotide.

26. A method of inhibiting the expression of human or mouse Apaf-1 in cells or tissues comprising contacting said cells or tissues in vitro with the compound of claim 3 so that expression of human or mouse Apaf-1 is inhibited.

* * * * *

SEQUENCE LISTING

<160> NUMBER OF SEQ ID NOS: 100

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg     20

<210> SEQ ID NO 2
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                              20

<210> SEQ ID NO 3
<211> LENGTH: 324
<212> TYPE: DNA
<213> ORGANISM: Homo sapiens
<220> FEATURE:

<400> SEQUENCE: 3
ggaggcgcct gtgaggcccg gacctgcccc ggggcgaagg gtatgtggcg agacagagcc     60
ctgcacccct aattcccggt ggaaaactcc tgttgccgtt tccctccacc ggcctggagt    120
ctcccagtct tgtcccggca gtgccgccct ccccactaag acctaggcgc aaaggcttgg    180
gtaagttgac ctcctcgctt ttctccccga gccaggttct ttggaggctt ggtagctgat    240
ttcagggact gagaatttga gacatggaat atttgataac cacctgctcc tgtcccagga    300
agaaaattct gttatgagga aatt                                         324

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
agagccctgc acccctaatt                                              20

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
tttgcgccta ggtcttagtg g                                            21

<210> SEQ ID NO 6
<211> LENGTH: 24
<212> TYPE: DNA
<213> ORGANISM: Artificial Sequence
<220> FEATURE:
<223> OTHER INFORMATION: PCR Probe

<400> SEQUENCE: 6
tctcccagtc ttgtcccggc agtg                                         24

<210> SEQ ID NO 7
<211> LENGTH: 21
<212> TYPE: DNA
<213> ORGANISM: Artificial Sequence
<220> FEATURE:
<223> OTHER INFORMATION: PCR Primer

<400> SEQUENCE: 7
caacggattt ggtcgtattg g                                            21
```

```
<210> SEQ ID NO 8
<211> LENGTH: 26
<212> TYPE: DNA
<213> ORGANISM: Artificial Sequence
<220> FEATURE:
<223> OTHER INFORMATION: PCR Primer

<400> SEQUENCE: 8
ggcaacaata tccactttac cagagt                                          26

<210> SEQ ID NO 9
<211> LENGTH: 21
<212> TYPE: DNA
<213> ORGANISM: Artificial Sequence
<220> FEATURE:
<223> OTHER INFORMATION: PCR Probe

<400> SEQUENCE: 9
cgcctggtca ccagggctgc t                                               21

<210> SEQ ID NO 10
<211> LENGTH: 5152
<212> TYPE: DNA
<213> ORGANISM: Mus musculus
<220> FEATURE:
<221> NAME/KEY: CDS
<222> LOCATION: (586)...(4302)

<400> SEQUENCE: 10
cggcttgagg cagagaccag gaggcagcta gaggagcaga cgtctcactc cgctcgcgga     60
agggtgtgag aggggtgtgt gggggtcggc agcgaggggt gtgtgccatc agccaccggc    120
gacgatctga dacagtcgca gcggctttcc gagcggcgtc cgcttcccgc ccgggcagct    180
cccgccagag gggtgaagcg gcgactggag tggccgtgct tttgtgccct gggtcccggt    240
accctcccct ggtgcggccc gaggcaagcc caccgaggtg accacccctc gacgccgctt    300
ggagatcccg ggcatccacc ctgcgccccg agcagctgat acccagggag gtgtcaggac    360
ctgcccgggg cgcggggtcg ccggaagcca ggcgggagcc ccggctgctt tctggcaatc    420
tagtctcata agtgaccctc cctgggctgc tttctttcga ttatcatcag tgaccctacc    480
ccggctgctc ttcccagcac aactccggtg caaaggcttg gcatcctgg tgctttgcct     540 ctagcccatg ctccacagcg aggagagaga aaccctgag gcaca atg gat gca aag    597
                                                 Met Asp Ala Lys
                                                  1 gcc cgc aat tgt ttg ctt caa cat aga gaa gct ttg gaa aag gac atc    645
Ala Arg Asn Cys Leu Leu Gln His Arg Glu Ala Leu Glu Lys Asp Ile
 5              10                  15                  20 aaa aca tcc tac atc atg gat cac atg atc agt aat ggc gtc ttg tca    693
Lys Thr Ser Tyr Ile Met Asp His Met Ile Ser Asn Gly Val Leu Ser
             25                  30                  35 gtg ata gag gag gag aag gtc aaa agt cag gcc act caa tat caa cga    741
Val Ile Glu Glu Glu Lys Val Lys Ser Gln Ala Thr Gln Tyr Gln Arg
         40                  45                  50 gca gcc gct tta att aaa atg ata ctt aat aaa gac aac tgt gcc tac    789
Ala Ala Ala Leu Ile Lys Met Ile Leu Asn Lys Asp Asn Cys Ala Tyr
     55                  60                  65 att tca ttc tac aac gct ctg cta cac gag ggc tat aag gac ctt gct    837
Ile Ser Phe Tyr Asn Ala Leu Leu His Glu Gly Tyr Lys Asp Leu Ala
 70                  75                  80 gcg ctt ctg cag agt ggc ctt cct ctt gtg tcg tct tcc agt gca agg    885
Ala Leu Leu Gln Ser Gly Leu Pro Leu Val Ser Ser Ser Ser Ala Arg
 85                  90                  95                 100
```

```
aca gtg ctg tgt gaa ggt gga gta ccc cag agg ccg gtt att ttc gtt    933
Thr Val Leu Cys Glu Gly Gly Val Pro Gln Arg Pro Val Ile Phe Val
            105                 110                 115 act aga aag aag ctg gtt cat gcg att cag cag aag ctc tgg aaa ctg    981
Thr Arg Lys Lys Leu Val His Ala Ile Gln Gln Lys Leu Trp Lys Leu
            120                 125                 130 aat gga gaa cca ggg tgg gtc acc atc tat ggg atg gca ggc tgc ggc   1029
Asn Gly Glu Pro Gly Trp Val Thr Ile Tyr Gly Met Ala Gly Cys Gly
            135                 140                 145 aag tct gtg tta gct gcg gaa gcc gtt cga gat cac tcc ctc tta gaa   1077
Lys Ser Val Leu Ala Ala Glu Ala Val Arg Asp His Ser Leu Leu Glu
    150                 155                 160 ggt tgc ttt tca ggg ggt gta cac tgg gtt tcc att gga aaa caa gac   1125
Gly Cys Phe Ser Gly Gly Val His Trp Val Ser Ile Gly Lys Gln Asp
165                 170                 175                 180 aaa tct ggg ctt ctc atg aaa ctg cag aat ctg tgc atg cgc ttg gac   1173
Lys Ser Gly Leu Leu Met Lys Leu Gln Asn Leu Cys Met Arg Leu Asp
            185                 190                 195 caa gat gag agt ttc tct cag agg ctt cca ctt aat att gag gag gcc   1221
Gln Asp Glu Ser Phe Ser Gln Arg Leu Pro Leu Asn Ile Glu Glu Ala
            200                 205                 210 aaa gac cgc ctc cgt gtt ctg atg ctg cgc aaa cac cca agg tct ctg   1269
Lys Asp Arg Leu Arg Val Leu Met Leu Arg Lys His Pro Arg Ser Leu
            215                 220                 225 ttg atc ttg gat gat gtt tgg gat cct tgg gtg tta aaa gct ttt gac   1317
Leu Ile Leu Asp Asp Val Trp Asp Pro Trp Val Leu Lys Ala Phe Asp
    230                 235                 240 aat cag tgt cag att ctt ctt acg acc aga gat aag agt gtt aca gat   1365
Asn Gln Cys Gln Ile Leu Leu Thr Thr Arg Asp Lys Ser Val Thr Asp
245                 250                 255                 260 tca gta atg ggt cct aag cat gtt gtc cct gtg gag agt ggt cta ggg   1413
Ser Val Met Gly Pro Lys His Val Val Pro Val Glu Ser Gly Leu Gly
                265                 270                 275 aga gag aaa gga ctt gag atc ttg tca ctt ttt gtt aat atg aag aaa   1461
Arg Glu Lys Gly Leu Glu Ile Leu Ser Leu Phe Val Asn Met Lys Lys
            280                 285                 290 gaa gat ctg cca gcg gag gct cac agt att ata aag gaa tgc aaa ggt   1509
Glu Asp Leu Pro Ala Glu Ala His Ser Ile Ile Lys Glu Cys Lys Gly
            295                 300                 305 tct cct ctt gta gtg tct tta att ggt gca ctt tta cgt gat ttt ccc   1557
Ser Pro Leu Val Val Ser Leu Ile Gly Ala Leu Leu Arg Asp Phe Pro
    310                 315                 320 aat cgc tgg gcg tac tac ctc aga cag ctt cag aat aag cag ttt aag   1605
Asn Arg Trp Ala Tyr Tyr Leu Arg Gln Leu Gln Asn Lys Gln Phe Lys
325                 330                 335                 340 aga ata agg aag tct tca tct tat gat tat gag gct cta gat gaa gcc   1653
Arg Ile Arg Lys Ser Ser Ser Tyr Asp Tyr Glu Ala Leu Asp Glu Ala
                345                 350                 355 atg tcg ata agt gtt gaa atg ctc aga gaa gac atc aaa gac tat tac   1701
Met Ser Ile Ser Val Glu Met Leu Arg Glu Asp Ile Lys Asp Tyr Tyr
            360                 365                 370 aca gac ctt tcc atc ctt cag aag gac gtc aag gta cct aca aag gtg   1749
Thr Asp Leu Ser Ile Leu Gln Lys Asp Val Lys Val Pro Thr Lys Val
            375                 380                 385 ttg tgc gtt ctc tgg gac ttg gaa acg gaa gaa gtt gaa gac atc ctg   1797
Leu Cys Val Leu Trp Asp Leu Glu Thr Glu Glu Val Glu Asp Ile Leu
    390                 395                 400 cag gag ttc gtt aat aag tct ctc tta ttc tgt aat cgg aat gga aag   1845
Gln Glu Phe Val Asn Lys Ser Leu Leu Phe Cys Asn Arg Asn Gly Lys
```

```
        405                 410                 415                 420
tca ttt tgt tat tat tta cac gat ctt caa gta gat ttt ctt aca gag              1893
Ser Phe Cys Tyr Tyr Leu His Asp Leu Gln Val Asp Phe Leu Thr Glu
                        425                 430                 435 aag aat cgc agt cag ctt cag gat ctg cac agg aag atg gtc act cag              1941
Lys Asn Arg Ser Gln Leu Gln Asp Leu His Arg Lys Met Val Thr Gln
                440                 445                 450 ttt cag agg tat tac cag ccc cac acg ctg tct cca gac cag gag gac              1989
Phe Gln Arg Tyr Tyr Gln Pro His Thr Leu Ser Pro Asp Gln Glu Asp
            455                 460                 465 tgc atg tat tgg tac aac ttc cta gcc tat cac atg gct agt gcc aat              2037
Cys Met Tyr Trp Tyr Asn Phe Leu Ala Tyr His Met Ala Ser Ala Asn
        470                 475                 480 atg cac aaa gaa ctt tgt gct tta atg ttt tcc ctg gac tgg att aaa              2085
Met His Lys Glu Leu Cys Ala Leu Met Phe Ser Leu Asp Trp Ile Lys
485                 490                 495                 500 gca aaa aca gaa ctt gtc ggc cct gcc cat ctg att cac gag ttc gtg              2133
Ala Lys Thr Glu Leu Val Gly Pro Ala His Leu Ile His Glu Phe Val
                    505                 510                 515 gca tat agg cat ata ttg gat gaa aag gat tgt gca gtc tgt gag aat              2181
Ala Tyr Arg His Ile Leu Asp Glu Lys Asp Cys Ala Val Cys Glu Asn
                520                 525                 530 ttt caa gag ttt tta tct tta aat gga cac ctc ctt gga cga cag cca              2229
Phe Gln Glu Phe Leu Ser Leu Asn Gly His Leu Leu Gly Arg Gln Pro
            535                 540                 545 ttt cct aat att gta cag ctg ggc ctc tgt gaa cca gaa act tcc gaa              2277
Phe Pro Asn Ile Val Gln Leu Gly Leu Cys Glu Pro Glu Thr Ser Glu
        550                 555                 560 gtt tat cga caa gca aag ctg cag gcc aag cag gag ggg gat act ggg              2325
Val Tyr Arg Gln Ala Lys Leu Gln Ala Lys Gln Glu Gly Asp Thr Gly
565                 570                 575                 580 ccg ctt tac ctg gaa tgg ata aac aaa aaa act atc aag aat ctg tcc              2373
Pro Leu Tyr Leu Glu Trp Ile Asn Lys Lys Thr Ile Lys Asn Leu Ser
                    585                 590                 595 cgc tta gtc gtc cgc ccc cac aca gat gct gtt tac cac gcg tgt ttt              2421
Arg Leu Val Val Arg Pro His Thr Asp Ala Val Tyr His Ala Cys Phe
                600                 605                 610 tct cag gat ggc cag aga ata gct tct tgt ggg gct gat aaa acc tta              2469
Ser Gln Asp Gly Gln Arg Ile Ala Ser Cys Gly Ala Asp Lys Thr Leu
            615                 620                 625 cag gtg ttc aaa gcc gag aca gga gag aaa ctt ctt gac att aaa gct              2517
Gln Val Phe Lys Ala Glu Thr Gly Glu Lys Leu Leu Asp Ile Lys Ala
        630                 635                 640 cat gaa gat gag gtg ctc tgc tgc gcg ttc tcc tca gac gac agt tac              2565
His Glu Asp Glu Val Leu Cys Cys Ala Phe Ser Ser Asp Asp Ser Tyr
645                 650                 655                 660 ata gcg acc tgc tca gcg gat aag aag gtt aag att tgg gat tct gcg              2613
Ile Ala Thr Cys Ser Ala Asp Lys Lys Val Lys Ile Trp Asp Ser Ala
                    665                 670                 675 act ggg aag ctt gtg cac acc tac gac gag cac tcg gag caa gtc aat              2661
Thr Gly Lys Leu Val His Thr Tyr Asp Glu His Ser Glu Gln Val Asn
                680                 685                 690 tgc tgc cat ttc acc aac agt agt aac cac ctt ctc ttg gcc acc ggg              2709
Cys Cys His Phe Thr Asn Ser Ser Asn His Leu Leu Leu Ala Thr Gly
            695                 700                 705 tca aat gat ttc ttc ctc aag ctc tgg gat ttg aat caa aaa gaa tgt              2757
Ser Asn Asp Phe Phe Leu Lys Leu Trp Asp Leu Asn Gln Lys Glu Cys
        710                 715                 720 cga aat acc atg ttt ggt cac acg aac tca gtc aac cac tgc agg ttc              2805
```

```
Arg Asn Thr Met Phe Gly His Thr Asn Ser Val Asn His Cys Arg Phe
725             730             735             740 tca cca gac gat gag ctc ttg gct agc tgc tca gct gac ggg act tta    2853
Ser Pro Asp Asp Glu Leu Leu Ala Ser Cys Ser Ala Asp Gly Thr Leu
            745             750             755 agg ctt tgg gat gtg aga tca gca aac gag agg aaa agc att aat gtg    2901
Arg Leu Trp Asp Val Arg Ser Ala Asn Glu Arg Lys Ser Ile Asn Val
            760             765             770 aag cgc ttc ttc ctg agt tca gaa gac cct cca gag gat gtg gag gtg    2949
Lys Arg Phe Phe Leu Ser Ser Glu Asp Pro Pro Glu Asp Val Glu Val
            775             780             785 atc gtg aag tgt tgt tcc tgg tct gca gat ggt gac aaa ata ata gtg    2997
Ile Val Lys Cys Cys Ser Trp Ser Ala Asp Gly Asp Lys Ile Ile Val
    790             795             800 gca gca aaa aac aaa gtc ctc ctt ttt gat att cat act agt ggc cta    3045
Ala Ala Lys Asn Lys Val Leu Leu Phe Asp Ile His Thr Ser Gly Leu
805             810             815             820 ttg gca gag atc cac aca ggc cat cac agc acc atc cag tac tgt gac    3093
Leu Ala Glu Ile His Thr Gly His His Ser Thr Ile Gln Tyr Cys Asp
            825             830             835 ttc tcc ccc tat gac cat ttg gct gtg att gcc ctg tct cag tac tgt    3141
Phe Ser Pro Tyr Asp His Leu Ala Val Ile Ala Leu Ser Gln Tyr Cys
            840             845             850 gtg gag ttg tgg aac ata gac tcc cgc cta aag gtg gcc gac tgc aga    3189
Val Glu Leu Trp Asn Ile Asp Ser Arg Leu Lys Val Ala Asp Cys Arg
            855             860             865 gga cat ttg agt tgg gtt cac ggt gtg atg ttt tct ccc gat ggc tcc    3237
Gly His Leu Ser Trp Val His Gly Val Met Phe Ser Pro Asp Gly Ser
870             875             880 tca ttt ttg aca gct tct gat gac caa aca ata agg gtc tgg gag aca    3285
Ser Phe Leu Thr Ala Ser Asp Asp Gln Thr Ile Arg Val Trp Glu Thr
885             890             895             900 aaa aag gta tgc aag aac tct gct atc gtg cta aag cag gaa ata gac    3333
Lys Lys Val Cys Lys Asn Ser Ala Ile Val Leu Lys Gln Glu Ile Asp
            905             910             915 gtc gtg ttt caa gag aac gaa acg atg gtc ctt gca gtt gac aac ata    3381
Val Val Phe Gln Glu Asn Glu Thr Met Val Leu Ala Val Asp Asn Ile
            920             925             930 aga ggc ctg caa ctc att gct gga aaa aca ggc cag att gat tac ctg    3429
Arg Gly Leu Gln Leu Ile Ala Gly Lys Thr Gly Gln Ile Asp Tyr Leu
            935             940             945 cct gaa gcc caa gtg agt tgc tgc tgc ctc agt cca cac ctt gag tac    3477
Pro Glu Ala Gln Val Ser Cys Cys Cys Leu Ser Pro His Leu Glu Tyr
950             955             960 gtg gca ttc gga gat gaa gat gga gcc att aag att ata gaa ctt cca    3525
Val Ala Phe Gly Asp Glu Asp Gly Ala Ile Lys Ile Ile Glu Leu Pro
965             970             975             980 aac aac aga gtc ttc agt tct ggg gtt ggg cac aag aaa gct gtg cgg    3573
Asn Asn Arg Val Phe Ser Ser Gly Val Gly His Lys Lys Ala Val Arg
            985             990             995 cac atc cag ttc aca gct gat ggg aag aca ctg att tca agt tct gaa    3621
His Ile Gln Phe Thr Ala Asp Gly Lys Thr Leu Ile Ser Ser Ser Glu
            1000            1005            1010 gat tct gtg att cag gta tgg aat tgg cag aca ggg gac tat gta ttt    3669
Asp Ser Val Ile Gln Val Trp Asn Trp Gln Thr Gly Asp Tyr Val Phe
            1015            1020            1025 ttg caa gcc cac cag gaa acg gta aag gac ttc agg ctc ctc caa gat    3717
Leu Gln Ala His Gln Glu Thr Val Lys Asp Phe Arg Leu Leu Gln Asp
            1030            1035            1040
```

-continued

| | |
|---|---|
| tca aga ttg ctt tct tgg tca ttt gat gga acg gtg aag gtg tgg aat<br>Ser Arg Leu Leu Ser Trp Ser Phe Asp Gly Thr Val Lys Val Trp Asn<br>1045                1050                    1055              1060 | 3765 |
| gtc att acc gga aga ata gaa aga gac ttt act tgt cat cag ggc aca<br>Val Ile Thr Gly Arg Ile Glu Arg Asp Phe Thr Cys His Gln Gly Thr<br>              1065                  1070              1075 | 3813 |
| gtg ctt tcc tgt gct atc tct tct gat gcg acc aag ttt tcc tct acc<br>Val Leu Ser Cys Ala Ile Ser Ser Asp Ala Thr Lys Phe Ser Ser Thr<br>              1080                  1085              1090 | 3861 |
| tct gct gat aag act gcc aag atc tgg agt ttt gac ctc ctt tcc cct<br>Ser Ala Asp Lys Thr Ala Lys Ile Trp Ser Phe Asp Leu Leu Ser Pro<br>         1095                  1100              1105 | 3909 |
| ctt cat gag ctg aag ggc cat aat ggc tgt gtc cgc tgc tct gcc ttc<br>Leu His Glu Leu Lys Gly His Asn Gly Cys Val Arg Cys Ser Ala Phe<br>        1110                  1115              1120 | 3957 |
| tcg ctg gat ggc atc ctg ttg gca act gga gat gac aat gga gaa atc<br>Ser Leu Asp Gly Ile Leu Leu Ala Thr Gly Asp Asp Asn Gly Glu Ile<br>1125                1130                  1135              1140 | 4005 |
| cgg ata tgg aat gtc tca gat ggc cag ctt ctt cat tcg tgt gct ccg<br>Arg Ile Trp Asn Val Ser Asp Gly Gln Leu Leu His Ser Cys Ala Pro<br>              1145                  1150              1155 | 4053 |
| atc tcg gta gag gaa gga act gct acc cac ggc ggc tgg gta act gat<br>Ile Ser Val Glu Glu Gly Thr Ala Thr His Gly Gly Trp Val Thr Asp<br>        1160                  1165              1170 | 4101 |
| gtg tgc ttc tct ccc gac agt aaa acg ctt gtc tct gct gga gga tat<br>Val Cys Phe Ser Pro Asp Ser Lys Thr Leu Val Ser Ala Gly Gly Tyr<br>1175                1180                  1185 | 4149 |
| ctc aag tgg tgg aat gtt gcc act ggg gac tcc tca cag acc ttc tac<br>Leu Lys Trp Trp Asn Val Ala Thr Gly Asp Ser Ser Gln Thr Phe Tyr<br>        1190                  1195              1200 | 4197 |
| aca aat gga aca aac ctc aag aaa atc cac gtg tcc cct gac ttc aga<br>Thr Asn Gly Thr Asn Leu Lys Lys Ile His Val Ser Pro Asp Phe Arg<br>1205                1210                  1215              1220 | 4245 |
| acc tat gtg act gtc gat aat ctc ggt att tta tat att tta cag gtt<br>Thr Tyr Val Thr Val Asp Asn Leu Gly Ile Leu Tyr Ile Leu Gln Val<br>              1225                  1230              1235 | 4293 |
| tta gag taa aatggctaag cgttaatgta gttcagcttc cttaagtttg aattggaaaa<br>Leu Glu | 4352 |
| aatctaaacc ctctatatca acttttataa agctgtgaat tgtactgcag tattgcaaca | 4412 |
| tttacaaagg tggtttaaca gctgggccag tgctctgtat agttgggtga atcatagtat | 4472 |
| atctccacaa aggaacatac ttttactcta ttttttttaaa tatagtcatc attgttatta | 4532 |
| acagtttgtc cttaacatgc aaatgaaatg gtaaatatgt accttgttat gctattggta | 4592 |
| aattctttga tgcattcaaa ttggttggca aaattagtga gaatcatttg aaggccttct | 4652 |
| ataggttgat gctgtcatta tgtaggctat gtcccaaggt aatggtggtc agttttctga | 4712 |
| accacactta ctcccagggg gtatggtttt ccaaataaat catgcttatt tgcactcttt | 4772 |
| aaatttgctt taagatattg tgtcatggtg caagcacagt ctgcaacatt tctcttgtta | 4832 |
| actcagtgag tattggtttt caacagttct tcctatgagc tagtcatgtg ttagagagat | 4892 |
| ttctctctgt agctctgtgt ttagctggac tctggctgtc agtgtctgtg aattgggcac | 4952 |
| caaccacctt gcactctttt agttgtttcg tttataaaga cagggtttat gtagtcctgg | 5012 |
| ctctcttggc actcagcatg tacaccaggt tagccttgaa ctcagagctc agcctgcctc | 5072 |
| tctgcctcct gagttctgga attgaaggcg tgtgccaaca gcacctctct ctctcagtta | 5132 |
| tactcgactg agcttgaccc | 5152 |

```
<210> SEQ ID NO 11
<211> LENGTH: 23
<212> TYPE: DNA
<213> ORGANISM: Artificial Sequence
<220> FEATURE:
<223> OTHER INFORMATION: PCR Primer

<400> SEQUENCE: 11
aagcaggaaa tagacgtcgt gtt                                               23

<210> SEQ ID NO 12
<211> LENGTH: 23
<212> TYPE: DNA
<213> ORGANISM: Artificial Sequence
<220> FEATURE:
<223> OTHER INFORMATION: PCR Primer

<400> SEQUENCE: 12
caatgagttg caggcctctt atg                                               23

<210> SEQ ID NO 13
<211> LENGTH: 26
<212> TYPE: DNA
<213> ORGANISM: Artificial Sequence
<220> FEATURE:
<223> OTHER INFORMATION: PCR Probe

<400> SEQUENCE: 13
tgtcaactgc aaggaccatc gtttcg                                            26

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
ggcaaattca acggcacagt                                                   20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
gggtctcgct cctggaagct                                                   20

<210> SEQ ID NO 16
<211> LENGTH: 27
<212> TYPE: DNA
<213> ORGANISM: Artificial Sequence
<220> FEATURE:
<223> OTHER INFORMATION: PCR Probe

<400> SEQUENCE: 16
aaggccgaga atgggaagct tgtcatc                                           27

<210> SEQ ID NO 17
<211> LENGTH: 3747
<212> TYPE: DNA
<213> ORGANISM: Homo sapiens
<220> FEATURE:
<221> NAME/KEY: CDS
```

-continued

```
<222> LOCATION: (1)...(3747)

<400> SEQUENCE: 17 atg gat gca aaa gct cga aat tgt ttg ctt caa cat aga gaa gct ctg        48
Met Asp Ala Lys Ala Arg Asn Cys Leu Leu Gln His Arg Glu Ala Leu
  1               5                  10                  15 gaa aag gac atc aag aca tcc tac atc atg gat cac atg att agt gat        96
Glu Lys Asp Ile Lys Thr Ser Tyr Ile Met Asp His Met Ile Ser Asp
             20                  25                  30 gga ttt tta aca ata tca gaa gag gaa aaa gta aga aat gag ccc act       144
Gly Phe Leu Thr Ile Ser Glu Glu Glu Lys Val Arg Asn Glu Pro Thr
         35                  40                  45 caa cag caa aga gca gct atg ctg att aaa atg ata ctt aaa aaa gat       192
Gln Gln Gln Arg Ala Ala Met Leu Ile Lys Met Ile Leu Lys Lys Asp
     50                  55                  60 aat gat tcc tac gta tca ttc tac aat gct cta cta cat gaa gga tat       240
Asn Asp Ser Tyr Val Ser Phe Tyr Asn Ala Leu Leu His Glu Gly Tyr
 65                  70                  75                  80 aaa gat ctt gct gcc ctt ctc cat gat ggc att cct gtt gtc tct tct       288
Lys Asp Leu Ala Ala Leu Leu His Asp Gly Ile Pro Val Val Ser Ser
                 85                  90                  95 tcc agt ggt aaa gat tca gtt agt gga ata act tcg tat gta agg aca       336
Ser Ser Gly Lys Asp Ser Val Ser Gly Ile Thr Ser Tyr Val Arg Thr
            100                 105                 110 gtc ctg tgt gaa ggt gga gta cca cag agg cca gtt gtt ttt gtc aca       384
Val Leu Cys Glu Gly Gly Val Pro Gln Arg Pro Val Val Phe Val Thr
        115                 120                 125 agg aag aag ctg gtg aat gca att cag cag aag ctc tcc aaa ttg aaa       432
Arg Lys Lys Leu Val Asn Ala Ile Gln Gln Lys Leu Ser Lys Leu Lys
    130                 135                 140 ggt gaa cca gga tgg gtc acc ata cat gga atg gca ggc tgt ggg aag       480
Gly Glu Pro Gly Trp Val Thr Ile His Gly Met Ala Gly Cys Gly Lys
145                 150                 155                 160 tct gta tta gct gca gaa gct gtt aga gat cat tcc ctt tta gaa ggt       528
Ser Val Leu Ala Ala Glu Ala Val Arg Asp His Ser Leu Leu Glu Gly
                165                 170                 175 tgt ttc cca ggg gga gtg cat tgg gtt tca gtt ggg aaa caa gac aaa       576
Cys Phe Pro Gly Gly Val His Trp Val Ser Val Gly Lys Gln Asp Lys
            180                 185                 190 tct ggg ctt ctg atg aaa ctg cag aat ctt tgc aca cgg ttg gat cag       624
Ser Gly Leu Leu Met Lys Leu Gln Asn Leu Cys Thr Arg Leu Asp Gln
        195                 200                 205 gat gag agt ttt tcc cag agg ctt cca ctt aat att gaa gag gct aaa       672
Asp Glu Ser Phe Ser Gln Arg Leu Pro Leu Asn Ile Glu Glu Ala Lys
    210                 215                 220 gac cgt ctc cgc att ctg atg ctt cgc aaa cac cca agg tct ctc ttg       720
Asp Arg Leu Arg Ile Leu Met Leu Arg Lys His Pro Arg Ser Leu Leu
225                 230                 235                 240 atc ttg gat gat gtt tgg gac tct tgg gtg ttg aaa gct ttt gac agt       768
Ile Leu Asp Asp Val Trp Asp Ser Trp Val Leu Lys Ala Phe Asp Ser
                245                 250                 255 cag tgt cag att ctt ctt aca acc aga gac aag agt gtt aca gat tca       816
Gln Cys Gln Ile Leu Leu Thr Thr Arg Asp Lys Ser Val Thr Asp Ser
            260                 265                 270 gta atg ggt cct aaa tat gta gtc cct gtg gag agt tcc tta gga aag       864
Val Met Gly Pro Lys Tyr Val Val Pro Val Glu Ser Ser Leu Gly Lys
        275                 280                 285 gaa aaa gga ctt gaa att tta tcc ctt ttt gtt aat atg aag aag gca       912
Glu Lys Gly Leu Glu Ile Leu Ser Leu Phe Val Asn Met Lys Lys Ala
    290                 295                 300
```

```
gat ttg cca gaa caa gct cat agt att ata aaa gaa tgt aaa ggc tct      960
Asp Leu Pro Glu Gln Ala His Ser Ile Ile Lys Glu Cys Lys Gly Ser
305             310                 315                 320 ccc ctt gta gta tct tta att ggt gca ctt tta cgt gat ttt ccc aat     1008
Pro Leu Val Val Ser Leu Ile Gly Ala Leu Leu Arg Asp Phe Pro Asn
                325                 330                 335 cgc tgg gag tac tac ctc aaa cag ctt cag aat aag cag ttt aag aga     1056
Arg Trp Glu Tyr Tyr Leu Lys Gln Leu Gln Asn Lys Gln Phe Lys Arg
            340                 345                 350 ata agg aaa tct tcg tct tat gat tat gag gct cta gat gaa gcc atg     1104
Ile Arg Lys Ser Ser Ser Tyr Asp Tyr Glu Ala Leu Asp Glu Ala Met
        355                 360                 365 tct ata agt gtt gaa atg ctc aga gaa gac atc aaa gat tat tac aca     1152
Ser Ile Ser Val Glu Met Leu Arg Glu Asp Ile Lys Asp Tyr Tyr Thr
370                 375                 380 gat ctt tcc atc ctt cag aag gac gtt aag gtg cct aca aag gtg tta     1200
Asp Leu Ser Ile Leu Gln Lys Asp Val Lys Val Pro Thr Lys Val Leu
385                 390                 395                 400 tgt att ctc tgg gac atg gaa act gaa gaa gtt gaa gac ata ctg cag     1248
Cys Ile Leu Trp Asp Met Glu Thr Glu Glu Val Glu Asp Ile Leu Gln
                405                 410                 415 gag ttt gta aat aag tct ctt tta ttc tgt gat cgg aat gga aag tcg     1296
Glu Phe Val Asn Lys Ser Leu Leu Phe Cys Asp Arg Asn Gly Lys Ser
            420                 425                 430 ttt cgt tat tat tta cat gat ctt caa gta gat ttt ctt aca gag aag     1344
Phe Arg Tyr Tyr Leu His Asp Leu Gln Val Asp Phe Leu Thr Glu Lys
        435                 440                 445 aat tgc agc cag ctt cag gat cta cat aag aag ata atc act cag ttt     1392
Asn Cys Ser Gln Leu Gln Asp Leu His Lys Lys Ile Ile Thr Gln Phe
450                 455                 460 cag aga tat cac cag ccg cat act ctt tca cca gat cag gaa gac tgt     1440
Gln Arg Tyr His Gln Pro His Thr Leu Ser Pro Asp Gln Glu Asp Cys
465                 470                 475                 480 atg tat tgg tac aac ttt ctg gcc tat cac atg gcc agt gcc aag atg     1488
Met Tyr Trp Tyr Asn Phe Leu Ala Tyr His Met Ala Ser Ala Lys Met
                485                 490                 495 cac aag gaa ctt tgt gct tta atg ttt tcc ctg gat tgg att aaa gca     1536
His Lys Glu Leu Cys Ala Leu Met Phe Ser Leu Asp Trp Ile Lys Ala
            500                 505                 510 aaa aca gaa ctt gta ggc cct gct cat ctg att cat gaa ttt gtg gaa     1584
Lys Thr Glu Leu Val Gly Pro Ala His Leu Ile His Glu Phe Val Glu
        515                 520                 525 tac aga cat ata cta gat gaa aag gat tgt gca gtc agt gag aat ttt     1632
Tyr Arg His Ile Leu Asp Glu Lys Asp Cys Ala Val Ser Glu Asn Phe
530                 535                 540 cag gag ttt tta tct tta aat gga cac ctt ctt gga cga cag cca ttt     1680
Gln Glu Phe Leu Ser Leu Asn Gly His Leu Leu Gly Arg Gln Pro Phe
545                 550                 555                 560 cct aat att gta caa ctg ggt ctc tgt gag ccg gaa act tca gaa gtt     1728
Pro Asn Ile Val Gln Leu Gly Leu Cys Glu Pro Glu Thr Ser Glu Val
                565                 570                 575 tat cag caa gct aag ctg cag gcc aag cag gag gtc gat aat gga atg     1776
Tyr Gln Gln Ala Lys Leu Gln Ala Lys Gln Glu Val Asp Asn Gly Met
            580                 585                 590 ctt tac ctg gaa tgg ata aac aaa aaa aac atc acg aat ctt tcc cgc     1824
Leu Tyr Leu Glu Trp Ile Asn Lys Lys Asn Ile Thr Asn Leu Ser Arg
        595                 600                 605 tta gtt gtc cgc ccc cac aca gat gct gtt tac cat gcc tgc ttt tct     1872
Leu Val Val Arg Pro His Thr Asp Ala Val Tyr His Ala Cys Phe Ser
```

```
            610                 615                 620
gag gat ggt cag aga ata gct tct tgt gga gct gat aaa acc tta cag    1920
Glu Asp Gly Gln Arg Ile Ala Ser Cys Gly Ala Asp Lys Thr Leu Gln
625                 630                 635                 640 gtg ttc aaa gct gaa aca gga gag aaa ctt cta gaa atc aag gct cat    1968
Val Phe Lys Ala Glu Thr Gly Glu Lys Leu Leu Glu Ile Lys Ala His
                645                 650                 655 gag gat gaa gtg ctt tgt tgt gca ttc tct aca gat gac aga ttt ata    2016
Glu Asp Glu Val Leu Cys Cys Ala Phe Ser Thr Asp Asp Arg Phe Ile
            660                 665                 670 gca acc tgc tca gtg gat aaa aaa gtg aag att tgg aat tct atg act    2064
Ala Thr Cys Ser Val Asp Lys Lys Val Lys Ile Trp Asn Ser Met Thr
        675                 680                 685 ggg gaa cta gta cac acc tat gat gag cac tca gag caa gtc aat tgc    2112
Gly Glu Leu Val His Thr Tyr Asp Glu His Ser Glu Gln Val Asn Cys
    690                 695                 700 tgc cat ttc acc aac agt agt cat cat ctt ctc tta gcc act ggg tca    2160
Cys His Phe Thr Asn Ser Ser His His Leu Leu Leu Ala Thr Gly Ser
705                 710                 715                 720 agt gac tgc ttc ctc aaa ctt tgg gat ttg aat caa aaa gaa tgt cga    2208
Ser Asp Cys Phe Leu Lys Leu Trp Asp Leu Asn Gln Lys Glu Cys Arg
                725                 730                 735 aat acc atg ttt ggt cat aca aat tca gtc aat cac tgc aga ttt tca    2256
Asn Thr Met Phe Gly His Thr Asn Ser Val Asn His Cys Arg Phe Ser
            740                 745                 750 cca gat gat aag ctt ttg gct agt tgt tca gct gat gga acc tta aag    2304
Pro Asp Asp Lys Leu Leu Ala Ser Cys Ser Ala Asp Gly Thr Leu Lys
        755                 760                 765 ctt tgg gat gcg aca tca gca aat gag agg aaa agc att aat gtg aaa    2352
Leu Trp Asp Ala Thr Ser Ala Asn Glu Arg Lys Ser Ile Asn Val Lys
    770                 775                 780 cag ttc ttc cta aat ttg gag gac cct caa gag gat atg gaa gtg ata    2400
Gln Phe Phe Leu Asn Leu Glu Asp Pro Gln Glu Asp Met Glu Val Ile
785                 790                 795                 800 gtg aag tgt tgt tcg tgg tct gct gat ggt gca agg ata atg gtg gca    2448
Val Lys Cys Cys Ser Trp Ser Ala Asp Gly Ala Arg Ile Met Val Ala
                805                 810                 815 gca aaa aat aaa atc ttt ctt ttt gac att cat act agt ggc cta ttg    2496
Ala Lys Asn Lys Ile Phe Leu Phe Asp Ile His Thr Ser Gly Leu Leu
            820                 825                 830 gga gaa atc cac acg ggc cat cac agc acc atc cag tac tgt gac ttc    2544
Gly Glu Ile His Thr Gly His His Ser Thr Ile Gln Tyr Cys Asp Phe
        835                 840                 845 tcc cca caa aac cat ttg gca gtg gtt gct ttg tcc cag tac tgt gta    2592
Ser Pro Gln Asn His Leu Ala Val Val Ala Leu Ser Gln Tyr Cys Val
    850                 855                 860 gag ttg tgg aat aca gac tca cgt tca aag gtg gct gat tgc aga gga    2640
Glu Leu Trp Asn Thr Asp Ser Arg Ser Lys Val Ala Asp Cys Arg Gly
865                 870                 875                 880 cat tta agt tgg gtt cat ggt gtg atg ttt tct cct gat gga tca tca    2688
His Leu Ser Trp Val His Gly Val Met Phe Ser Pro Asp Gly Ser Ser
                885                 890                 895 ttt ttg aca tct tct gat gac cag aca atc agg ctc tgg gag aca aag    2736
Phe Leu Thr Ser Ser Asp Asp Gln Thr Ile Arg Leu Trp Glu Thr Lys
            900                 905                 910 aaa gta tgt aag aac tct gct gta atg tta aag caa gaa gta gat gtt    2784
Lys Val Cys Lys Asn Ser Ala Val Met Leu Lys Gln Glu Val Asp Val
        915                 920                 925 gtg ttt caa gaa aat gaa gtg atg gtc ctt gca gtt gac cat ata aga    2832
```

```
                                                                -continued

Val Phe Gln Glu Asn Glu Val Met Val Leu Ala Val Asp His Ile Arg
    930                 935                 940 cgt ctg caa ctc att aat gga aga aca ggt cag att gat tat ctg act      2880
Arg Leu Gln Leu Ile Asn Gly Arg Thr Gly Gln Ile Asp Tyr Leu Thr
945                 950                 955                 960 gaa gct caa gtt agc tgc tgt tgc tta agt cca cat ctt cag tac att      2928
Glu Ala Gln Val Ser Cys Cys Cys Leu Ser Pro His Leu Gln Tyr Ile
                965                 970                 975 gca ttt gga gat gaa aat gga gcc att gag att tta gaa ctt gta aac      2976
Ala Phe Gly Asp Glu Asn Gly Ala Ile Glu Ile Leu Glu Leu Val Asn
    980                 985                 990 aat aga atc ttc cag tcc agg ttt cag cac aag aaa act gta tgg cac      3024
Asn Arg Ile Phe Gln Ser Arg Phe Gln His Lys Lys Thr Val Trp His
        995                 1000                1005 atc cag ttc aca gcc gat gag aag act ctt att tca agt tct gat gat      3072
Ile Gln Phe Thr Ala Asp Glu Lys Thr Leu Ile Ser Ser Ser Asp Asp
    1010                1015                1020 gct gaa att cag gta tgg aat tgg caa ttg gac aaa tgt atc ttt cta      3120
Ala Glu Ile Gln Val Trp Asn Trp Gln Leu Asp Lys Cys Ile Phe Leu
1025                1030                1035                1040 cga ggc cat cag gaa aca gtg aaa gac ttt aga ctc ttg aaa aat tca      3168
Arg Gly His Gln Glu Thr Val Lys Asp Phe Arg Leu Leu Lys Asn Ser
                1045                1050                1055 aga ctg ctt tct tgg tca ttt gat gga aca gtg aag gta tgg aat att      3216
Arg Leu Leu Ser Trp Ser Phe Asp Gly Thr Val Lys Val Trp Asn Ile
            1060                1065                1070 att act gga aat aaa gaa aaa gac ttt gtc tgt cac cag ggt aca gta      3264
Ile Thr Gly Asn Lys Glu Lys Asp Phe Val Cys His Gln Gly Thr Val
    1075                1080                1085 ctt tct tgt gac att tct cac gat gct acc aag ttt tca tct acc tct      3312
Leu Ser Cys Asp Ile Ser His Asp Ala Thr Lys Phe Ser Ser Thr Ser
1090                1095                1100 gct gac aag act gca aag atc tgg agt ttt gat ctc ctt ttg cca ctt      3360
Ala Asp Lys Thr Ala Lys Ile Trp Ser Phe Asp Leu Leu Leu Pro Leu
1105                1110                1115                1120 cat gaa ttg agg ggc cac aac ggc tgt gtg cgc tgc tct gcc ttc tct      3408
His Glu Leu Arg Gly His Asn Gly Cys Val Arg Cys Ser Ala Phe Ser
                1125                1130                1135 gtg gac agt acc ctg ctg gca acg gga gat gac aat gga gaa atc agg      3456
Val Asp Ser Thr Leu Leu Ala Thr Gly Asp Asp Asn Gly Glu Ile Arg
            1140                1145                1150 ata tgg aat gtc tca aac ggt gag ctt ctt cat ttg tgt gct ccg ctt      3504
Ile Trp Asn Val Ser Asn Gly Glu Leu Leu His Leu Cys Ala Pro Leu
    1155                1160                1165 tca gaa gaa gga gct gct acc cat gga ggc tgg gtg act gac ctt tgc      3552
Ser Glu Glu Gly Ala Ala Thr His Gly Gly Trp Val Thr Asp Leu Cys
1170                1175                1180 ttt tct cca gat ggc aaa atg ctt atc tct gct gga gga tat att aag      3600
Phe Ser Pro Asp Gly Lys Met Leu Ile Ser Ala Gly Gly Tyr Ile Lys
1185                1190                1195                1200 tgg tgg aac gtt gtc act ggg gaa tcc tca cag acc ttc tac aca aat      3648
Trp Trp Asn Val Val Thr Gly Glu Ser Ser Gln Thr Phe Tyr Thr Asn
                1205                1210                1215 gga acc aat ctt aag aaa ata cac gtg tcc cct gac ttc aaa aca tat      3696
Gly Thr Asn Leu Lys Lys Ile His Val Ser Pro Asp Phe Lys Thr Tyr
            1220                1225                1230 gtg act gtg gat aat ctt ggt att tta tat att tta cag act tta gaa      3744
Val Thr Val Asp Asn Leu Gly Ile Leu Tyr Ile Leu Gln Thr Leu Glu
    1235                1240                1245
``` taa 3747

<210> SEQ ID NO 18
<211> LENGTH: 454
<212> TYPE: DNA
<213> ORGANISM: Homo sapiens
<220> FEATURE:
<223> OTHER INFORMATION:
<221> NAME/KEY: unsure
<222> LOCATION: 285
<223> OTHER INFORMATION: unknown

<400> SEQUENCE: 18

```
aaaaacagaa cttgtaggcc ctgctcatct gattcatgaa tttgtggaat acagacatat    60
actagatgaa aaggtatata tattaacatg aaaaattagt gctaaaaagg aatctcattt   120
tttttttacat ttaattctag atttaatgat gggaatgagc agaatagaag gggtgaagat  180
aatttccctc ctttgatttt tggttattct aattaatttg cttcctaccc tactgggaaa   240
gtaggtagga ttgaagttta aaagctagga aaataagatg ttcantggtt tttttaaaaa   300
aagaatgtat taagaaatgt gtttgataat gagatttttta ccctatgttt aaaagtccga  360
agaagattac tatatatttg ttacttaatg gttggctgtt caatttttagt tcatataaag  420
aatatttcat ttaagctttt aaagtggcca gatc                               454
```

<210> SEQ ID NO 19
<211> LENGTH: 605
<212> TYPE: DNA
<213> ORGANISM: Homo sapiens
<220> FEATURE:
<223> OTHER INFORMATION:
<221> NAME/KEY: unsure
<222> LOCATION: 553
<223> OTHER INFORMATION: unknown
<221> NAME/KEY: unsure
<222> LOCATION: 555
<223> OTHER INFORMATION: unknown

<400> SEQUENCE: 19

```
aagtttatcg gcaagctaag ctgcaggcca agcaggaggt cgataatgga atgctttacc    60
tggaatggat gtaagtaggt taggagagaa accaaaggga gtggtgcgct aactatatca   120
ttatttttca ggtggtgaat acgatcactc caggaggatt taactacttt cgaaagggct   180
ggaacttttta ataagcattc ttacttattg aaaagttcta gagaagtaag cataggagaa   240
aatgattgta ttttcaaaga atccatataa atagatgcct gtaaggcatt tggacaaatt   300
atcctaagta ttcagtacta agtgcttgac ttactgtaat ttagtatagt ggtgaggagc   360
atggactttg gagccacaga actgggtttg agcctcagtt ctaaaaccta ataattctgt   420
gactttgaac aagttacagg ttttttctctc atatgtaaaa tggagataac aacctttgaa   480
ataagtgctg tttccatgaa gatttatta ttatttattt atttattttg agacagatct    540
cctatgttgc cangntggat gcattggtgt gatcttggtc actgcacctc tgctcccgga   600
tcaac                                                                605
```

<210> SEQ ID NO 20
<211> LENGTH: 491
<212> TYPE: DNA
<213> ORGANISM: Homo sapiens

<400> SEQUENCE: 20

```
aagtccacat cttcagtaca ttgcatttgg agatgaaaat ggagccattg aggtattcag    60
```

```
tgctagtctt cagaatcttt ctgtacagaa ttaaataaaa ctaattatat gtctggcatt      120
gtgcacttct attttttattt attttttattt ttgaaatggg gtcttgctgt gtcacccacg    180
ctgagtacag tgacacgatc acagccgact gcagccttga ccttctgagc tcaagtgatt     240
ttcccactta agcctcctga gtagctggga ctaaaggtgt acgtcaccat gcccgactaa     300 ttttttttttt tttgtagaat gggtccctgt gttgcccagg ctggtctcaa actcctgggt    360
ttaagcgatt gtccggcctc agcctcccaa agtgtgggga ttataggcat gggaactttt    420
gtgcctggct attgtttacc tttttttttt tgaatcaagg atccaccttg tttgcacagg    480
ctggaatgca a                                                          491

<210> SEQ ID NO 21
<211> LENGTH: 7042
<212> TYPE: DNA
<213> ORGANISM: Homo sapiens
<220> FEATURE:
<221> NAME/KEY: CDS
<222> LOCATION: (578)...(4162)

<400> SEQUENCE: 21
aagaagaggt agcgagtgga cgtgactgct ctatcccggg caaaagggat agaaccagag       60
gtggggagtc tgggcagtcg gcgacccgcg aagacttgag gtgccgcagc ggcatccgga      120
gtagcgccgg gctccctccg gggtgcagcc gccgtcgggg aagggcgcc acaggccggg       180 aagacctcct cccttttgtgt ccagtagtgg ggtccaccgg agggcggccc gtgggccggg    240
cctcaccgcg gcgctccggg actgtggggt caggctgcgt tgggtggacg cccacctcgc    300
caaccttcgg aggtccctgg gggtcttcgt gcgcccggg gctgcagaga tccaggggag     360
gcgcctgtga ggcccggacc tgccccgggg cgaagggtat gtggcgagac agagccctgc    420 accctaatt cccggtggaa aactcctgtt gccgtttccc tccaccggcc tggagtctcc    480
cagtcttgtc ccggcagtgc cgccctcccc actaagacct aggcgcaaag gcttggctca    540
tggttgacag ctcagagaga gaaagatctg agggaag atg gat gca aaa gct cga      595
                                          Met Asp Ala Lys Ala Arg
                                           1               5 aat tgt ttg ctt caa cat aga gaa gct ctg gaa aag gac atc aag aca       643
Asn Cys Leu Leu Gln His Arg Glu Ala Leu Glu Lys Asp Ile Lys Thr
         10                  15                  20 tcc tac atc atg gat cac atg att agt gat gga ttt tta aca ata tca      691
Ser Tyr Ile Met Asp His Met Ile Ser Asp Gly Phe Leu Thr Ile Ser
     25                  30                  35 gaa gag gaa aaa gta aga aat gag ccc act caa cag caa aga gca gct      739
Glu Glu Glu Lys Val Arg Asn Glu Pro Thr Gln Gln Gln Arg Ala Ala
 40                  45                  50 atg ctg att aaa atg ata ctt aaa aaa gat aat gat tcc tac gta tca      787
Met Leu Ile Lys Met Ile Leu Lys Lys Asp Asn Asp Ser Tyr Val Ser
55                  60                  65                  70 ttc tac aat gct cta cta cat gaa gga tat aaa gat ctt gct gcc ctt      835
Phe Tyr Asn Ala Leu Leu His Glu Gly Tyr Lys Asp Leu Ala Ala Leu
                 75                  80                  85 ctc cat gat ggc att cct gtt gtc tct tct tcc agt gta agg aca gtc      883
Leu His Asp Gly Ile Pro Val Val Ser Ser Ser Ser Val Arg Thr Val
             90                  95                 100 ctg tgt gaa ggt gga gta cca cag agg cca gtt gtt ttt gtc aca agg      931
Leu Cys Glu Gly Gly Val Pro Gln Arg Pro Val Val Phe Val Thr Arg
        105                 110                 115 aag aag ctg gtg aat gca att cag cag aag ctc tcc aaa ttg aaa ggt      979
Lys Lys Leu Val Asn Ala Ile Gln Gln Lys Leu Ser Lys Leu Lys Gly
```

```
              120                 125                 130
gaa cca gga tgg gtc acc ata cat gga atg gca ggc tgt ggg aag tct      1027
Glu Pro Gly Trp Val Thr Ile His Gly Met Ala Gly Cys Gly Lys Ser
135                 140                 145                 150 gta tta gct gca gaa gct gtt aga gat cat tcc ctt tta gaa ggt tgt      1075
Val Leu Ala Ala Glu Ala Val Arg Asp His Ser Leu Leu Glu Gly Cys
                155                 160                 165 ttc cca ggg gga gtg cat tgg gtt tca gtt ggg aaa caa gac aaa tct      1123
Phe Pro Gly Gly Val His Trp Val Ser Val Gly Lys Gln Asp Lys Ser
            170                 175                 180 ggg ctt ctg atg aaa ctg cag aat ctt tgc aca cgg ttg gat cag gat      1171
Gly Leu Leu Met Lys Leu Gln Asn Leu Cys Thr Arg Leu Asp Gln Asp
        185                 190                 195 gag agt ttt tcc cag agg ctt cca ctt aat att gaa gag gct aaa gac      1219
Glu Ser Phe Ser Gln Arg Leu Pro Leu Asn Ile Glu Glu Ala Lys Asp
    200                 205                 210 cgt ctc cgc att ctg atg ctt cgc aaa cac cca agg tct ctc ttg atc      1267
Arg Leu Arg Ile Leu Met Leu Arg Lys His Pro Arg Ser Leu Leu Ile
215                 220                 225                 230 ttg gat gat gtt tgg gac tct tgg gtg ttg aaa gct ttt gac agt cag      1315
Leu Asp Asp Val Trp Asp Ser Trp Val Leu Lys Ala Phe Asp Ser Gln
                235                 240                 245 tgt cag att ctt ctt aca acc aga gac aag agt gtt aca gat tca gta      1363
Cys Gln Ile Leu Leu Thr Thr Arg Asp Lys Ser Val Thr Asp Ser Val
            250                 255                 260 atg ggt cct aaa tat gta gtc cct gtg gag agt tcc tta gga aag gaa      1411
Met Gly Pro Lys Tyr Val Val Pro Val Glu Ser Ser Leu Gly Lys Glu
        265                 270                 275 aaa gga ctt gaa att tta tcc ctt ttt gtt aat atg aag aag gca gat      1459
Lys Gly Leu Glu Ile Leu Ser Leu Phe Val Asn Met Lys Lys Ala Asp
    280                 285                 290 ttg cca gaa caa gct cat agt att ata aaa gaa tgt aaa ggc tct ccc      1507
Leu Pro Glu Gln Ala His Ser Ile Ile Lys Glu Cys Lys Gly Ser Pro
295                 300                 305                 310 ctt gta gta tct tta att ggt gca ctt tta cgt gat ttt ccc aat cgc      1555
Leu Val Val Ser Leu Ile Gly Ala Leu Leu Arg Asp Phe Pro Asn Arg
                315                 320                 325 tgg gag tac tac ctc aaa cag ctt cag aat aag cag ttt aag aga ata      1603
Trp Glu Tyr Tyr Leu Lys Gln Leu Gln Asn Lys Gln Phe Lys Arg Ile
            330                 335                 340 agg aaa tct tcg tct tat gat tat gag gct cta gat gaa gcc atg tct      1651
Arg Lys Ser Ser Ser Tyr Asp Tyr Glu Ala Leu Asp Glu Ala Met Ser
        345                 350                 355 ata agt gtt gaa atg ctc aga gaa gac atc aaa gat tat tac aca gat      1699
Ile Ser Val Glu Met Leu Arg Glu Asp Ile Lys Asp Tyr Tyr Thr Asp
    360                 365                 370 ctt tcc atc ctt cag aag gac gtt aag gtg cct aca aag gtg tta tgt      1747
Leu Ser Ile Leu Gln Lys Asp Val Lys Val Pro Thr Lys Val Leu Cys
375                 380                 385                 390 att ctc tgg gac atg gaa act gaa gaa gtt gaa gac ata ctg cag gag      1795
Ile Leu Trp Asp Met Glu Thr Glu Glu Val Glu Asp Ile Leu Gln Glu
                395                 400                 405 ttt gta aat aag tct ctt tta ttc tgt gat cgg aat gga aag tcg ttt      1843
Phe Val Asn Lys Ser Leu Leu Phe Cys Asp Arg Asn Gly Lys Ser Phe
            410                 415                 420 cgt tat tat tta cat gat ctt caa gta gat ttt ctt aca gag aag aat      1891
Arg Tyr Tyr Leu His Asp Leu Gln Val Asp Phe Leu Thr Glu Lys Asn
        425                 430                 435 tgc agc cag ctt cag gat cta cat aag aag ata atc act cag ttt cag      1939
```

```
Cys Ser Gln Leu Gln Asp Leu His Lys Lys Ile Ile Thr Gln Phe Gln
    440                 445                 450 aga tat cac cag ccg cat act ctt tca cca gat cag gaa gac tgt atg       1987
Arg Tyr His Gln Pro His Thr Leu Ser Pro Asp Gln Glu Asp Cys Met
455                 460                 465                 470 tat tgg tac aac ttt ctg gcc tat cac atg gcc agt gcc aag atg cac       2035
Tyr Trp Tyr Asn Phe Leu Ala Tyr His Met Ala Ser Ala Lys Met His
                475                 480                 485 aag gaa ctt tgt gct tta atg ttt tcc ctg gat tgg att aaa gca aaa       2083
Lys Glu Leu Cys Ala Leu Met Phe Ser Leu Asp Trp Ile Lys Ala Lys
            490                 495                 500 aca gaa ctt gta ggc cct gct cat ctg att cat gaa ttt gtg gaa tac       2131
Thr Glu Leu Val Gly Pro Ala His Leu Ile His Glu Phe Val Glu Tyr
        505                 510                 515 aga cat ata cta gat gaa aag gat tgt gca gtc agt gag aat ttt cag       2179
Arg His Ile Leu Asp Glu Lys Asp Cys Ala Val Ser Glu Asn Phe Gln
    520                 525                 530 gag ttt tta tct tta aat gga cac ctt ctt gga cga cag cca ttt cct       2227
Glu Phe Leu Ser Leu Asn Gly His Leu Leu Gly Arg Gln Pro Phe Pro
535                 540                 545                 550 aat att gta caa ctg ggt ctc tgt gag ccg gaa act tca gaa gtt tat       2275
Asn Ile Val Gln Leu Gly Leu Cys Glu Pro Glu Thr Ser Glu Val Tyr
                555                 560                 565 cag caa gct aag ctg cag gcc aag cag gag gtc gat aat gga atg ctt       2323
Gln Gln Ala Lys Leu Gln Ala Lys Gln Glu Val Asp Asn Gly Met Leu
            570                 575                 580 tac ctg gaa tgg ata aac aaa aaa aac atc acg aat ctt tcc cgc tta       2371
Tyr Leu Glu Trp Ile Asn Lys Lys Asn Ile Thr Asn Leu Ser Arg Leu
        585                 590                 595 gtt gtc cgc ccc cac aca gat gct gtt tac cat gcc tgc ttt tct gag       2419
Val Val Arg Pro His Thr Asp Ala Val Tyr His Ala Cys Phe Ser Glu
    600                 605                 610 gat ggt cag aga ata gct tct tgt gga gct gat aaa acc tta cag gtg       2467
Asp Gly Gln Arg Ile Ala Ser Cys Gly Ala Asp Lys Thr Leu Gln Val
615                 620                 625                 630 ttc aaa gct gaa aca gga gag aaa ctt cta gaa atc aag gct cat gag       2515
Phe Lys Ala Glu Thr Gly Glu Lys Leu Leu Glu Ile Lys Ala His Glu
                635                 640                 645 gat gaa gtg ctt tgt tgt gca ttc tct aca gat gac aga ttt ata gca       2563
Asp Glu Val Leu Cys Cys Ala Phe Ser Thr Asp Asp Arg Phe Ile Ala
            650                 655                 660 acc tgc tca gtg gat aaa aaa gtg aag att tgg aat tct atg act ggg       2611
Thr Cys Ser Val Asp Lys Lys Val Lys Ile Trp Asn Ser Met Thr Gly
        665                 670                 675 gaa cta gta cac acc tat gat gag cac tca gag caa gtc aat tgc tgc       2659
Glu Leu Val His Thr Tyr Asp Glu His Ser Glu Gln Val Asn Cys Cys
    680                 685                 690 cat ttc acc aac agt agt cat cat ctt ctc tta gcc act ggg tca agt       2707
His Phe Thr Asn Ser Ser His His Leu Leu Leu Ala Thr Gly Ser Ser
695                 700                 705                 710 gac tgc ttc ctc aaa ctt tgg gat ttg aat caa aaa gaa tgt cga aat       2755
Asp Cys Phe Leu Lys Leu Trp Asp Leu Asn Gln Lys Glu Cys Arg Asn
                715                 720                 725 acc atg ttt ggt cat aca aat tca gtc aat cac tgc aga ttt tca cca       2803
Thr Met Phe Gly His Thr Asn Ser Val Asn His Cys Arg Phe Ser Pro
            730                 735                 740 gat gat aag ctt ttg gct agt tgt tca gct gat gga acc tta aag ctt       2851
Asp Asp Lys Leu Leu Ala Ser Cys Ser Ala Asp Gly Thr Leu Lys Leu
        745                 750                 755
```

-continued

| | |
|---|---|
| tgg gat gcg aca tca gca aat gag agg aaa agc att aat gtg aaa cag<br>Trp Asp Ala Thr Ser Ala Asn Glu Arg Lys Ser Ile Asn Val Lys Gln<br>760                        765                        770 | 2899 |
| ttc ttc cta aat ttg gag gac cct caa gag gat atg gaa gtg ata gtg<br>Phe Phe Leu Asn Leu Glu Asp Pro Gln Glu Asp Met Glu Val Ile Val<br>775                        780                        785                        790 | 2947 |
| aag tgt tgt tcg tgg tct gct gat ggt gca agg ata atg gtg gca gca<br>Lys Cys Cys Ser Trp Ser Ala Asp Gly Ala Arg Ile Met Val Ala Ala<br>                        795                        800                        805 | 2995 |
| aaa aat aaa atc ttt ttg tgg aat aca gac tca cgt tca aag gtg gct<br>Lys Asn Lys Ile Phe Leu Trp Asn Thr Asp Ser Arg Ser Lys Val Ala<br>          810                        815                        820 | 3043 |
| gat tgc aga gga cat tta agt tgg gtt cat ggt gtg atg ttt tct cct<br>Asp Cys Arg Gly His Leu Ser Trp Val His Gly Val Met Phe Ser Pro<br>          825                        830                        835 | 3091 |
| gat gga tca tca ttt ttg aca tct tct gat gac cag aca atc agg ctc<br>Asp Gly Ser Ser Phe Leu Thr Ser Ser Asp Asp Gln Thr Ile Arg Leu<br>          840                        845                        850 | 3139 |
| tgg gag aca aag aaa gta tgt aag aac tct gct gta atg tta aag caa<br>Trp Glu Thr Lys Lys Val Cys Lys Asn Ser Ala Val Met Leu Lys Gln<br>855                        860                        865                        870 | 3187 |
| gaa gta gat gtt gtg ttt caa gaa aat gaa gtg atg gtc ctt gca gtt<br>Glu Val Asp Val Val Phe Gln Glu Asn Glu Val Met Val Leu Ala Val<br>                        875                        880                        885 | 3235 |
| gac cat ata aga cgt ctg caa ctc att aat gga aga aca ggt cag att<br>Asp His Ile Arg Arg Leu Gln Leu Ile Asn Gly Arg Thr Gly Gln Ile<br>          890                        895                        900 | 3283 |
| gat tat ctg act gaa gct caa gtt agc tgc tgt tgc tta agt cca cat<br>Asp Tyr Leu Thr Glu Ala Gln Val Ser Cys Cys Cys Leu Ser Pro His<br>          905                        910                        915 | 3331 |
| ctt cag tac att gca ttt gga gat gaa aat gga gcc att gag att tta<br>Leu Gln Tyr Ile Ala Phe Gly Asp Glu Asn Gly Ala Ile Glu Ile Leu<br>920                        925                        930 | 3379 |
| gaa ctt gta aac aat aga atc ttc cag tcc agg ttt cag cac aag aaa<br>Glu Leu Val Asn Asn Arg Ile Phe Gln Ser Arg Phe Gln His Lys Lys<br>935                        940                        945                        950 | 3427 |
| act gta tgg cac atc cag ttc aca gcc gat gag aag act ctt att tca<br>Thr Val Trp His Ile Gln Phe Thr Ala Asp Glu Lys Thr Leu Ile Ser<br>                        955                        960                        965 | 3475 |
| agt tct gat gat gct gaa att cag gta tgg aat tgg caa ttg gac aaa<br>Ser Ser Asp Asp Ala Glu Ile Gln Val Trp Asn Trp Gln Leu Asp Lys<br>          970                        975                        980 | 3523 |
| tgt atc ttt cta cga ggc cat cag gaa aca gtg aaa gac ttt aga ctc<br>Cys Ile Phe Leu Arg Gly His Gln Glu Thr Val Lys Asp Phe Arg Leu<br>          985                        990                        995 | 3571 |
| ttg aaa aat tca aga ctg ctt tct tgg tca ttt gat gga aca gtg aag<br>Leu Lys Asn Ser Arg Leu Leu Ser Trp Ser Phe Asp Gly Thr Val Lys<br>          1000                      1005                      1010 | 3619 |
| gta tgg aat att att act gga aat aaa gaa aaa gac ttt gtc tgt cac<br>Val Trp Asn Ile Ile Thr Gly Asn Lys Glu Lys Asp Phe Val Cys His<br>1015                      1020                      1025                      1030 | 3667 |
| cag ggt aca gta ctt tct tgt gac att tct cac gat gct acc aag ttt<br>Gln Gly Thr Val Leu Ser Cys Asp Ile Ser His Asp Ala Thr Lys Phe<br>          1035                      1040                      1045 | 3715 |
| tca tct acc tct gct gac aag act gca aag atc tgg agt ttt gat ctc<br>Ser Ser Thr Ser Ala Asp Lys Thr Ala Lys Ile Trp Ser Phe Asp Leu<br>          1050                      1055                      1060 | 3763 |
| ctt ttg cca ctt cat gaa ttg agg ggc cac aac ggc tgt gtg cgc tgc<br>Leu Leu Pro Leu His Glu Leu Arg Gly His Asn Gly Cys Val Arg Cys<br>          1065                      1070                      1075 | 3811 |

-continued

| | |
|---|---|
| tct gcc ttc tct gtg gac agt acc ctg ctg gca acg gga gat gac aat<br>Ser Ala Phe Ser Val Asp Ser Thr Leu Leu Ala Thr Gly Asp Asp Asn<br>1080              1085              1090 | 3859 |
| gga gaa atc agg ata tgg aat gtc tca aac ggt gag ctt ctt cat ttg<br>Gly Glu Ile Arg Ile Trp Asn Val Ser Asn Gly Glu Leu Leu His Leu<br>1095              1100              1105              1110 | 3907 |
| tgt gct ccg ctt tca gaa gaa gga gct gct acc cat gga ggc tgg gtg<br>Cys Ala Pro Leu Ser Glu Glu Gly Ala Ala Thr His Gly Gly Trp Val<br>              1115              1120              1125 | 3955 |
| act gac ctt tgc ttt tct cca gat ggc aaa atg ctt atc tct gct gga<br>Thr Asp Leu Cys Phe Ser Pro Asp Gly Lys Met Leu Ile Ser Ala Gly<br>              1130              1135              1140 | 4003 |
| gga tat att aag tgg tgg aac gtt gtc act ggg gaa tcc tca cag acc<br>Gly Tyr Ile Lys Trp Trp Asn Val Val Thr Gly Glu Ser Ser Gln Thr<br>              1145              1150              1155 | 4051 |
| ttc tac aca aat gga acc aat ctt aag aaa ata cac gtg tcc cct gac<br>Phe Tyr Thr Asn Gly Thr Asn Leu Lys Lys Ile His Val Ser Pro Asp<br>              1160              1165              1170 | 4099 |
| ttc aaa aca tat gtg act gtg gat aat ctt ggt att tta tat att tta<br>Phe Lys Thr Tyr Val Thr Val Asp Asn Leu Gly Ile Leu Tyr Ile Leu<br>1175              1180              1185              1190 | 4147 |
| cag act tta gaa taa aatagttaag cattaatgta gttgaacttt ttaaattttt<br>Gln Thr Leu Glu<br>              1195 | 4202 |
| gaattggaaa aaaattctaa tgaaaccctg atatcaactt tttataaagc tcttaattgt | 4262 |
| tgtgcagtat tgcattcatt acaaaagtgt ttgtggttgg atgaataata ttaatgtagc | 4322 |
| ttttcccaa atgaacatac ctttaatctt gttttcatg atcatcatta acagtttgtc | 4382 |
| cttaggatgc aaatgaaaat gtgaatacat accttgttgt actgttggta aaattctgtc | 4442 |
| ttgatgcatt caaatggtt gacataatta atgagaagaa tttggaagaa attggtattt | 4502 |
| taatactgtc tgtatttatt actgttatgc aggctgtgcc tcagggtagc agtggcctgc | 4562 |
| tttttgaacc acacttaccc caagggggtt ttgttctcct aaatacaatc ttagaggttt | 4622 |
| tttgcactct ttaaatttgc tttaaaaata ttgtgtctgt gtgcatagtc tgcagcattt | 4682 |
| cctttaattg actcaataag tgagtcttgg atttagcagg cccccccacc ttttttttt | 4742 |
| gttttggag acagagtctt gctttgttgc caggctggag tgcagtggcg cgatctcggc | 4802 |
| tcaccacaat cgctgcctcc tgggttcaag caattctcct gcctcagcct cccgagtagc | 4862 |
| tgggactaca ggtgtgcgca catgccaggc taattttgt attttagta gagacggggt | 4922 |
| ttcaccatgt tggccgggat ggtctcgatc tcttgacctc atgatctacc cgccttggcc | 4982 |
| tcccaaagtg ctgagattac aggcgtgagc caccgtgcct ggccaggccc cttctcttt | 5042 |
| aatggagaca gggtcttgca ctatcaccca ggctggagtg cagtggcata atcatacctc | 5102 |
| attgcagcct cagactcctg ggttcaagca atcctcctgc ctcagcctcc caagtagctg | 5162 |
| agactgcagg cacgagccac cacacccagc taattttaa gttttcttgt agagacaggg | 5222 |
| tctcactatg ttgtctaggc tggtcttgaa ctcttggcct caagtaatcc tcctgcctca | 5282 |
| gcctcccaaa gtgttgggat tgcagatatg agccactggc ctggccttca gcagttcttt | 5342 |
| ttgtgaagta aaacttgtat gttggaaaga gtagatttta ttggtctacc cttttctcac | 5402 |
| tgtagctgct ggcagccctg tgccatatct ggactctagt tgtcagtatc tgagttggac | 5462 |
| actattcctg ctccctcttg tttccttacat atcagacttc ttacttgaat gaaacctgat | 5522 |
| ctttcctaat cctcactttt ttctttttta aaaagcagtt tctccactgc taaatgttag | 5582 |

-continued

| | |
|---|---|
| tcattgaggt gggggccaatt ttaatcataa gccttaataa gattttttcta agaaatgtga | 5642 |
| aatagaacaa ttttcatcta attccattta cttttagatg aatggcattg tgaatgccat | 5702 |
| tcttttaatg aatttcaaga gaattctctg gttttctgtg taattccaga tgagtcactg | 5762 |
| taactctaga agattaacct tccagccaac ctattttcct ttcccttgtc tctctcatcc | 5822 |
| tcttttcctt ccttctttcc tttctcttct tttatctcca aggttaatca ggaaaaatag | 5882 |
| cttttgacag gggaaaaaac tcaataacta gctattttg acctcctgat caggaacttt | 5942 |
| agttgaagcg taaatctaaa gaaacatttt ctctgaaata tattattaag ggcaatggag | 6002 |
| ataaattaat agtagatgtg gttcccagaa aatataatca aaattcaaag attttttttg | 6062 |
| tttctgtaac tggaactaaa tcaaatgatt actagtgtta atagtagata acttgtttttt | 6122 |
| attgttggtg catattagta taactgtggg gtaggtcggg gagagggtaa gggaatagat | 6182 |
| cactcagatg tattttagat aagctattta gcctttgatg gaatcataaa tacagtgaat | 6242 |
| acaatccttt gcattgttaa ggaggttttt tgtttttaaa tggtgggtca aggagctagt | 6302 |
| ttacaggctt actgtgattt aagcaaatgt gaaaagtgaa accttaattt tatcaaaaga | 6362 |
| aatttctgta aatggtatgt ctccttagaa tacccaaatc ataatttat ttgtacacac | 6422 |
| tgttaggggc tcatctcatg taggcagagt ataaagtatt acctttgga attaaaagcc | 6482 |
| actgactgtt ataaagtata acaacacaca tcaggtttta aaaagccttg aatggcccctt | 6542 |
| gtcttaaaaa gaaattagga gccaggtgcg gtggcacgtg cctgtagtcc cagctccttg | 6602 |
| ggaggctgag acaggaggat tccttgagcc ctggagtttg agtccagcct gggtgacata | 6662 |
| gcaagaccct gtcttaaaag aaaaatggga agaaagacaa ggtaacatga agaaagaaga | 6722 |
| gatacctagt atgatggagc tgcaaatttc atggcagttc atgcagtcgg tcaagaggag | 6782 |
| gattttgttt tgtagtttgc agatgagcat ttctaaagca ttttcccttg ctgtattttt | 6842 |
| ttgtattata aattacattg gacttcatat atataattt tttttacatt atatgtctct | 6902 |
| tgtatgtttt gaaactcttg tatttatgat atagcttata tgattttttt gccttggtat | 6962 |
| acattttaaa atatgaattt aaaaaatttt tgtaaaaata aaattcacaa aattgttttg | 7022 |
| aaaaacaaaa aaaaaaaaaa | 7042 |

<210> SEQ ID NO 22
<211> LENGTH: 359
<212> TYPE: DNA
<213> ORGANISM: Homo sapiens

<400> SEQUENCE: 22

| | |
|---|---|
| cattatatgt ctcttgtatg ttttgaaact cttgtattta tgatatagct tatatgattt | 60 |
| ttttgccttg gtatacattt taaaatatga atttaaaaaa ttttttgtaaa aataaaattc | 120 |
| acaaaattgt tttgaaaaac attttttggat tgtttcattc tttgcttgtc atttatctgt | 180 |
| tgattagacc actaaagtga aggattcaag ctaaatacat caacctttct atttaggctt | 240 |
| tatcagctat atgtaaattc aattctatca aaattttctg agtgcctcct cagtgtgtct | 300 |
| ctctgatggt tcctgcccgg tatggctggc atgaagaaga tcctgtaaaa aagagaatt | 359 |

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
caggactgtc cttacatacg                                                    20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
caataggcca ctagtatgaa                                                    20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ctggatggtg ctgtgatggc                                                    20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
acagtactgg atggtgctgt                                                    20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
gggagaagtc acagtactgg                                                    20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
cccaagcctt tgcgcctagg                                                    20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
cataacagaa ttttcttcct                                                    20

<210> SEQ ID NO 30
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 30
aatgagattc cttttagca                                                    20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
tgaacatctt attttcctag                                                   20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
tatagtaatc ttcttcggac                                                   20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
aatcctcctg gagtgatcgt                                                   20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
atacctcaat ggctccattt                                                   20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gctgaggccg gacaatcgct                                                   20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ccccagggac ctccgaaggt                                                   20
```

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
caaccatgag ccaagccttt                                          20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tttgcatcca tcttccctca                                          20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
ctatgttgaa gcaaacaatt                                          20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
gcttctctat gttgaagcaa                                          20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
tcatgtgatc catgatgtag                                          20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
ggtactccac cttcacacag                                          20

<210> SEQ ID NO 43
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 43
agcccagatt tgtcttgttt                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
aatattaagt ggaagcctct                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
agagaccttg ggtgtttgcg                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
cccaaacatc atccaagatc                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
gtaagaagaa tctgacactg                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
actgaatctg taacactctt                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
cccattactg aatctgtaac                                              20
```

```
<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
ttaggaccca ttactgaatc                                                   20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
tatttaggac ccattactga                                                   20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
ttcttcatat taacaaaaag                                                   20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
cgtaaaagtg caccaattaa                                                   20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
ttgggaaaat cacgtaaaag                                                   20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
cagcgattgg gaaaatcacg                                                   20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 56
tcttaaactg cttattctga                                           20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
ccttattctc ttaaactgct                                           20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
tagagcctca taatcataag                                           20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ttcatctaga gcctcataat                                           20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
catggcttca tctagagcct                                           20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
tctgagcatt tcaacactta                                           20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
ttgatgtctt ctctgagcat                                           20

<210> SEQ ID NO 63
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 63
gtccttctga aggatggaaa                                                    20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
tacataacac ctttgtaggc                                                    20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
ctgtaagaaa atctacttga                                                    20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
tcttctctgt aagaaaatct                                                    20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
tccagggaaa acattaaagc                                                    20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ctgcacaatc cttttcatct                                                    20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
```

-continued actgcacaat ccttttcatc                                    20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
gtgtccattt aaagataaaa                                    20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
ggaaatggct gtcgtccaag                                    20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
tgtacaatat taggaaatgg                                    20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
tcctgcttgg cctgcagctt                                    20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tttatccatt ccaggtaaag                                    20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gtaaacagca tctgtgtggg                                    20

<210> SEQ ID NO 76
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 76
ccacaagaag ctattctctg                                          20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
acctgtaagg ttttatcagc                                          20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ttgaacacct gtaaggtttt                                          20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ctttgaacac ctgtaaggtt                                          20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
atggcagcaa ttgacttgct                                          20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
actgttggtg aaatggcagc                                          20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
gacattcttt ttgattcaaa                                          20
```

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
catggtattt cgacattctt                                              20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
accaaacatg gtatttcgac                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
catcccaaag ctttaaggtt                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
acattaatgc ttttcctctc                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
tctcccagag cctgattgtc                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
gttctaaaat ctcaatggct                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
tgccaattcc atacctgaat                                               20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
ttccatcaaa tgaccaagaa                                               20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
aactccagat ctttgcagtc                                               20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
atttctccat tgtcatctcc                                               20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
cgttccacca cttaatatat                                               20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
gtgtagaagg tctgtgagga                                               20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
ccatttgtgt agaaggtctg                                               20

<210> SEQ ID NO 96

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
aactatttta ttctaaagtc                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
gccaggccag tggctcatat                                              20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
cctcttgacc gactgcatga                                              20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
gaattttatt tttacaaaaa                                              20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
acactgagga ggcactcaga                                              20
```